United States Patent
Sager et al.

(10) Patent No.: US 9,633,548 B2
(45) Date of Patent: Apr. 25, 2017

(54) LEVERAGING A USER'S GEO-LOCATION TO ARM AND DISARM A NETWORK ENABLED DEVICE

(71) Applicant: Canary Connect, Inc., New York, NY (US)

(72) Inventors: Adam D. Sager, Englewood Cliffs, NJ (US); Chris I. Rill, Mamaroneck, NY (US)

(73) Assignee: Canary Connect, Inc., New York, NY (US)

( * ) Notice: Subject to any disclaimer, the term of this patent is extended or adjusted under 35 U.S.C. 154(b) by 0 days.

(21) Appl. No.: 14/260,260

(22) Filed: Apr. 23, 2014

(65) Prior Publication Data

US 2014/0320280 A1    Oct. 30, 2014

Related U.S. Application Data

(60) Provisional application No. 61/815,223, filed on Apr. 23, 2013.

(51) Int. Cl.
*G08B 23/00*  (2006.01)
*G08B 25/00*  (2006.01)
(Continued)

(52) U.S. Cl.
CPC .............. *G08B 25/008* (2013.01); *G01K 1/14* (2013.01); *G01N 33/0004* (2013.01); *G05B 15/02* (2013.01); *G08B 23/00* (2013.01); *G08B 25/00* (2013.01); *G08B 25/001* (2013.01); *G08B 25/003* (2013.01); *G08B 25/005* (2013.01); *G08B 25/006* (2013.01); *G08B 25/10* (2013.01);
(Continued)

(58) Field of Classification Search
CPC ...... G08B 25/00; G08B 23/00; G08B 25/001; G08B 25/003; G08B 25/10; G01K 1/14; G01N 33/0004
USPC ...... 340/501, 521, 517, 539.11, 539.19, 540, 340/541
See application file for complete search history.

(56) References Cited

U.S. PATENT DOCUMENTS 5,463,595 A * 10/1995 Rodhall ................ A01M 29/18
340/426.23
5,604,384 A *  2/1997 Carlo .................... B60R 25/045
180/287

(Continued)

OTHER PUBLICATIONS

International Search Report and Written Opinion for PCT Application No. PCT/US14/35208, issued on Dec. 2, 2014.

*Primary Examiner* — Eric M Blount
(74) *Attorney, Agent, or Firm* — Sheehan Phinney Bass & Green PA

(57) ABSTRACT

A method of controlling operation of a security device in a location by a mobile user device, comprises monitoring a region around a location of interest, via a mobile user device; providing at least one security device within the region, wherein the security device comprises at least one sensor to monitor a location. The user device recognizes that the user device has entered the region, and searches for a security device within the region. The security device is detected and at least certain security features and/or sensors are disarmed. Disarming may mean that at least certain notifications are not sent about the status of the location. When the user device recognizes that the device is leaving the region, security features and/or sensors may be armed.

26 Claims, 29 Drawing Sheets

(51) Int. Cl.
*G08B 25/10* (2006.01)
*H04L 12/24* (2006.01)
*H04W 12/06* (2009.01)
*G08C 19/00* (2006.01)
*G08C 17/02* (2006.01)
*G01K 1/14* (2006.01)
*G01N 33/00* (2006.01)
*G08B 27/00* (2006.01)
*H04Q 9/00* (2006.01)
*G05B 15/02* (2006.01)
*H04L 12/28* (2006.01)
*H04L 29/06* (2006.01)
*H04N 7/18* (2006.01)

(52) U.S. Cl.
CPC ......... *G08B 27/001* (2013.01); *G08B 27/006* (2013.01); *G08C 17/02* (2013.01); *G08C 19/00* (2013.01); *H04L 12/2827* (2013.01); *H04L 41/0803* (2013.01); *H04Q 9/00* (2013.01); *H04W 12/06* (2013.01); *G05B 2219/2642* (2013.01); *H04L 63/083* (2013.01); *H04N 7/183* (2013.01); *H04N 7/188* (2013.01); *H04Q 2209/823* (2013.01)

(56) References Cited

U.S. PATENT DOCUMENTS

| | | | |
|---|---|---|---|
| 5,850,180 A * | 12/1998 | Hess | G08B 7/06 340/539.1 |
| 7,015,806 B2 | 3/2006 | Naidoo | |
| 8,036,679 B1 | 10/2011 | Barbeau et al. | |
| 8,350,694 B1 * | 1/2013 | Trundle | G08B 25/08 340/539.11 |
| 8,531,294 B2 | 9/2013 | Slavin et al. | |
| 8,849,301 B2 | 9/2014 | Husney et al. | |
| 9,057,210 B2 * | 6/2015 | Dumas | G07C 9/00571 |
| 9,141,150 B1 | 9/2015 | Tundle et al. | |
| 9,154,001 B2 | 10/2015 | Dharwada et al. | |
| 9,208,676 B2 | 12/2015 | Fadell et al. | |
| 9,247,378 B2 | 1/2016 | Bisson et al. | |
| 2002/0147006 A1 * | 10/2002 | Coon | G08C 17/02 455/420 |
| 2003/0070102 A1 | 4/2003 | Kondo | |
| 2005/0046567 A1 | 3/2005 | Mortenson | |
| 2008/0036595 A1 * | 2/2008 | Hollstien | G08B 13/00 340/541 |
| 2009/0027495 A1 | 1/2009 | Oskin | |
| 2009/0203349 A1 * | 8/2009 | Hollstien | G08B 25/016 455/404.1 |
| 2012/0013443 A1 * | 1/2012 | Poder | G08B 13/2491 340/8.1 |
| 2012/0187513 A1 | 7/2012 | Holenarsipur | |
| 2012/0188081 A1 * | 7/2012 | Van Katwijk | G01S 13/56 340/541 |
| 2012/0274876 A1 | 11/2012 | Cappaert | |
| 2012/0309373 A1 | 12/2012 | Abogendia | |
| 2013/0189946 A1 | 7/2013 | Swanson | |
| 2014/0045482 A1 * | 2/2014 | Bisson | G05D 23/1905 455/420 |
| 2014/0228055 A1 | 8/2014 | Karaoguz | |
| 2014/0244710 A1 | 8/2014 | Sharma et al. | |
| 2014/0266669 A1 * | 9/2014 | Fadell | G05B 19/042 340/501 |
| 2014/0266699 A1 * | 9/2014 | Poder | G08B 25/001 340/539.13 |
| 2014/0320280 A1 | 10/2014 | Sager et al. | |
| 2015/0024781 A1 | 1/2015 | Konicek et al. | |
| 2015/0048927 A1 | 2/2015 | Simmons | |
| 2015/0161834 A1 | 6/2015 | Spahl | |
| 2015/0168002 A1 | 6/2015 | Plitkins et al. | |
| 2015/0312719 A1 | 10/2015 | Cho et al. | |
| 2015/0365787 A1 | 12/2015 | Farrell | |
| 2016/0012702 A1 | 1/2016 | Hart et al. | |

* cited by examiner

*820

NOTIFICATIONS

○ Thursday at 10:36 AM
Activity detected in Living Room at Brooklyn Apartment

○ Thursday at 7:36 AM
Activity and sound detected in Doorway at Brooklyn Apartment Thursday at 2:36 AM
Invitation from Rob Nyland
viewed by you Wednesday at 4:36 PM
Activity detected in Doorway at Home
viewed by you Wednesday at 5:36 PM

BROOKLYN APARTMENT
5:09 PM

FIG.26

LEVERAGING A USER'S GEO-LOCATION TO ARM AND DISARM A NETWORK ENABLED DEVICE

RELATED APPLICATION

The present application claims the benefit of U.S. Provisional Patent Application No. 61/815,223, which was filed on Apr. 23, 2013, is assigned to the assignee of the present application, and is incorporated by reference, herein.

FIELD OF THE INVENTION

Home security and monitoring devices and systems and, more particularly, home security and monitoring devices comprising a plurality of sensors, and systems having learning capabilities.

BACKGROUND OF THE INVENTION

Home security systems typically include a door alarm, which can trigger an audible sound, such as a siren, when the door is opened when the system is armed. The door alarm may be triggered when a contact between two surfaces is opened when the door is opened. Similar contacts may be provided on windows, to trigger an alarm when a window is opened when the system is armed. Sensors can also be provided to detect when the glass of a window is broken. Besides triggering a siren or other sound to warn occupants of the home, the home security system may inform a call center that an alarm has been triggered. A user may enter a code into a device that communicates with the call center, to inform the call center that an alarm is a false alarm. The call center may also call a home to inquire about an alarm. The call center may call the police if a user does not respond. Such home systems are prone to false alarms, which can be annoying to residents and neighbors, and waste the time and resources of authorities, such as the police and fire department. Other types of home security devices are also known, such as fire, smoke, and carbon monoxide detectors, for example. Often, such devices are managed and positioned by a user, and provide a siren or other such sound if triggered.

Webcams may be provided to monitor children, baby sitters, and other activities in a home. Webcams provide a large amount of often irrelevant video that needs to be reviewed, which can be time consuming even if using a fast forward function.

Home automation systems allow for remote control of lights, thermostats, and security devices.

SUMMARY OF THE INVENTION

There is no known integrated device comprising video and one or more sensors that can provide a more complete understanding of what is happening in a physical location, such as a home, office, or other location.

In accordance with an embodiment of the invention, a device may transmit audio, video, and/or sensor data within one or multiple streams, via Wifi or other wireless communications, simultaneously, to a processing system for analysis. The processing system may be a discrete entity or may be a cloud based system, for example. The sensors in the device may include a temperature sensor, humidity sensor, air quality sensor, motion detector, and/or other sensors, as described below. Since contemporaneous data from multiple or all of the sensors may be analyzed together, a more complete understanding of what is happening at a location may be developed than when data from a single sensor is analyzed, as in the known prior art. The device may include a camera (for video), a microphone (for audio), a passive infrared sensor (to detect motion), and life safety sensors, such as air quality monitoring sensors, carbon dioxide monitoring sensors, temperature monitoring sensors, humidity monitoring sensors and/or other air quality or atmospheric sensors, for example. A processing device is provided in the device, as well, and an additional processing device in the home is not needed.

Via the multiple sensors within one device, the device is able to combine the data feeds from the sensors simultaneously to create a clear picture of what is occurring in the one location. For instance, by putting a video feed in the same device as a temperature sensor, it can be determined whether movement of people or actions of people impacts the temperature of a given location. The device may gather precise readings because of the physical proximity of the device, and provide more accurate reading and more immediate data when including in the same data stream via a Wifi and/or cellular networks. Simultaneous sensor feeds also means that the user can have a complete picture of the audio, visual, and sensor readings from a physical place from any given time, and more accurately detect patterns of change, or impact from one sensor or activity on another sensor or activity.

In accordance with an embodiment of the invention, the combined functionality assists in determining what is ordinary and what is out-of-the-ordinary in a location. This assists in decreasing false alarms, and identifying events that a user wants and/or needs to be informed of.

Embodiments of the invention provide a network-based, such as a cloud-based, communal security layer to the Internet, powered by integrated and intelligent device/s used to connect people to their homes, other people, and places that are important to them, enabling peace-of-mind, a sense of safety, security, and a detection of situations that deviate from the norm.

In accordance with another embodiment of the invention, a virtual neighborhood community watch may be defined to enable groups of people to look after each other via alert and notification-based actions for preventing, reacting to, and responding to, life-safety events and other events, for example.

The combined functionality provides an exceptional perspective on what is happing in a location, specifically identifying both what is ordinary and out-of-the-ordinary. Likewise many of the individual elements of our invention, as outlined here, are new ways of dealing with old issues of security, connectivity, personal welfare, and safety.

In this regard, the security device facilitates user monitoring of a physical place, through the collection of continuous information from the location when the device is powered. This information is analyzed by the device and/or a processing system, such as a cloud based processing system, to determine if an event has occurred that is of interest to the user. A user may be one or more members of a household, for example. There may be a primary user or users, who receive initial notifications concerning events happening in a location and determine when notifications are to be sent, and backup users, designated by the primary users, to receive notifications when the primary user does not respond, for example.

An event of interest can be a negative event, such as a security or safety incident, including a life-threatening incident such as a fire or an attacker, for example. An event of interest may also be a neutral or positive incident, such as watching one's child. In accordance with embodiments of the invention, an event of interest may also be an event that is out of the ordinary, such as an unknown person entering the home or a known person entering the home at an unexpected time, for example. The overall importance of an incident may be determined both by an individual user as well as compiled information from a multitude of users. The device, therefore, acts as a portal connecting a physical place to the web and to internet/cloud-based services.

Events may be defined in multiple ways. For example, events may be defined by the system, by defining thresholds for temperature, rate of temperature change, air quality, or movement, for example. In defining events, the system may take into account crowd-sourced information collected from a large number of devices at a large number of locations, for example. The crowd-sourced information applied to a particular user may be derived from similarly situated users, such as users in one bedroom apartments in New York City, users in suburban homes outside of Washington D.C., etc. For example, based on crowd sourced information from locations near a particular user, the system 14 may learn and apply criteria, such as thresholds, for single sensors and combinations of sensors, for that user.

Events may also be defined by individual user input, allowing the user to essentially 'program' the device to learn the user's personal preferences and how they interact from a security and safety perspective. Users may provide input to the system to define normal or acceptable activities, and/or to confirm or modify system defined and/or crowd-sourced defined events.

In accordance with another embodiment of the invention, the device and/or system record a series of events, including data from a sensor (or multiple sensors) identified as of interest based on being above/below a threshold or an out of the ordinary event, for example. The data is then sent to the processing system, which determines, among other things, the time of day of the incident, who is in the home or location, or when the event happened. Individual notifications sent over the course of a day, for example, may be displayed to a user on a user device in the form of a timeline of events, so that a user can monitor the activities that have taken place in the location. This further assists the user in understanding what happens in a location.

In many homes, especially apartments or smaller units, a single security/monitoring device can be used. In larger locations, such as large rooms, hallways, and homes with multiple rooms, multiple devices can be used.

In embodiments of the invention, the device connects to a home network or directly to a user via their smartphone, other mobile device, and/or computer. The device may constantly be on and gathering data, which means that it will be a continual source of information for what is occurring in a single location, and for determining if anything is out of the ordinary. Alternatively, the user may turn off the device, when desired, either directly or remotely, via their smartphone, etc.

In accordance with embodiment of the invention, processing of collected data may take place on the device and/or in processing center. For example, relevant-confirming analytics can be performed from the device, such as through video, audio and motion sensing to determine whether an event might have taken place and the data should be sent to the processing center via the network for further analysis. The processing system then determines if an event or incident within the range of the device is of interest to the owner of the device, either by being a deviation from what is normal or by being another event that gives insight into what is taking place inside the home, for example. Inputs from one or more sensor may be used to determine if there is an incident or an event worth informing the owner of the device about, by receiving and analyzing sensor data from multiple sensors.

In embodiments of the invention, the processing system communicates through the network directly with a user or group of users, or to the user's backup friends or family, or to the designated government or private authorities, such as the police and fire department, who can assist the user in responding to the event. Notifications can come in the form of a direct communication such as an email, text message, or phone call, through a network-based portal dedicated to public safety officials or first responders, or through a software application, which is accessible by select individuals. Having immediate feedback from physical locations may greatly reduce the amount of time required for response and enables the authorities to help save lives.

In accordance with embodiments of the invention, the device does not require any installation or connection to a wall or wired home system. In addition, the device in accordance with certain embodiments does not require a professional installer, or any installation at all. It need not be connected to a wall or wired home system, although that is an option. The device does not need to be permanently or semi-permanently affixed to a surface, such as wall, doorframe, door, floor, ceiling, or a window, for example, although that is an option if desired. In accordance with an embodiment of the invention, it may be placed on a surface, such as the floor, a table, or a bookcase, for example.

In accordance with one embodiment, the device can be connected to the Internet through Wifi or through another network, such as a 3G or 4G service from a cellular operator, for example, and through that connection perform all of the necessary functions of a monitoring, security, and/or safety system, as well as of a home connected device.

DESCRIPTION OF THE FIGURES

FIG. 26 is a timeline of notifications, in accordance with an embodiment of the invention.

DETAILED DESCRIPTION

Figure 1:
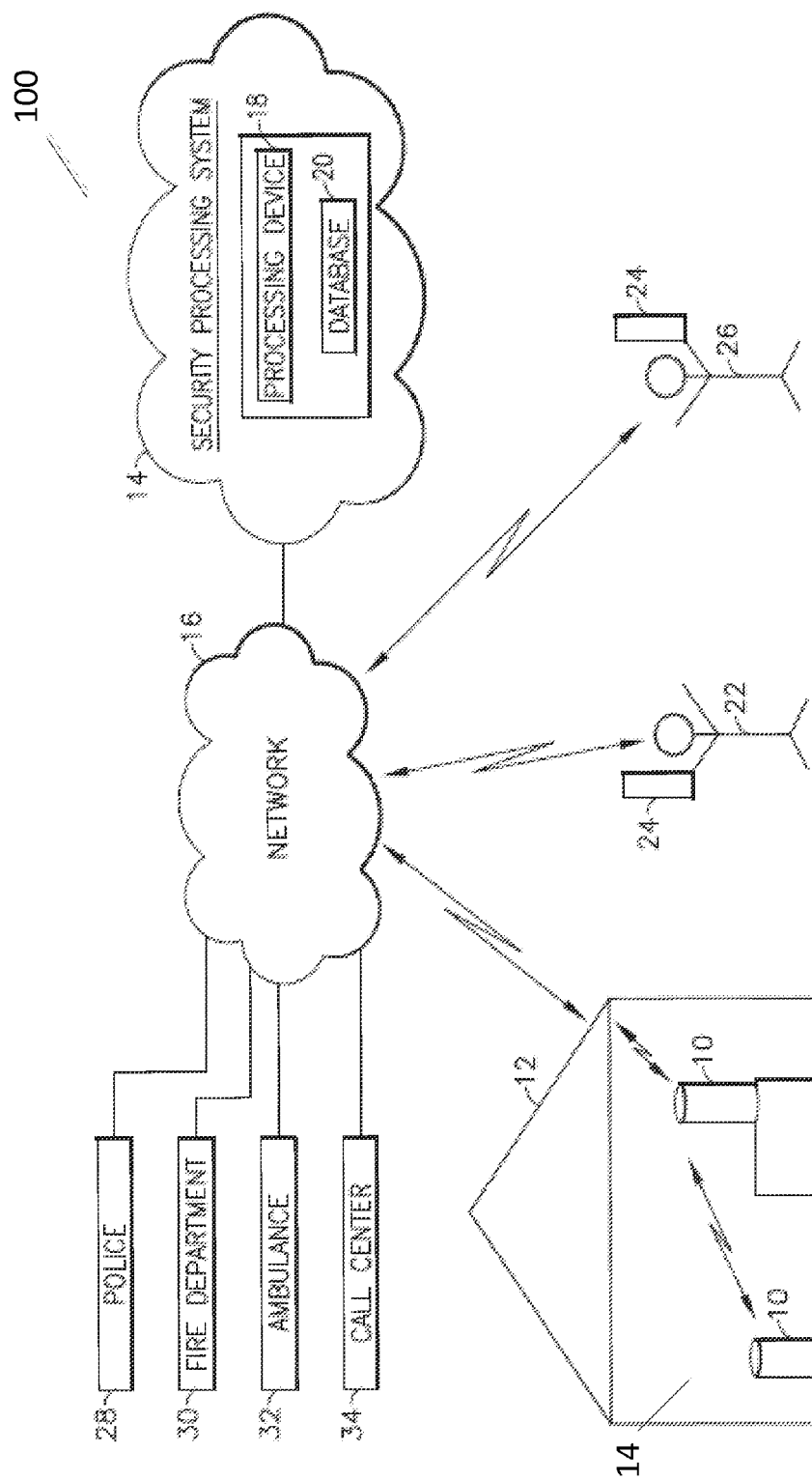
FIG. 1 is an example of a security system in accordance with an embodiment of the invention.

FIG. 1 is an example of a security system 100 in accordance with an embodiment of the invention. In this example, the system 100 comprises one or more monitoring/security devices 10, each positioned in one or more locations within a home 12. One or more devices 10 may be positioned within a single room 14 or in multiple rooms of the home 12, depending on the size of respective rooms, the areas of the home of activity and/or concern, the degree of security desired, the locations of entrances to the home, where children play, where a baby, children, older people, or sick people sleep, etc.

In the example of FIG. 1, one device is placed near a corner of the room 14, and the other is placed on a table near an opposite corner of in the same room. One or more devices may be placed in other rooms of the home, as well. Devices 10 may also be used in office buildings, stores, individual offices, hospital and hospice rooms, and any other locations that would be desirable to monitor and/or home security concerns. For example, devices 10 may also be placed in outdoor locations, such as backyards, decks, patios, etc. As noted above, installation is not required to attach the device 10 to a wall, doorframe, door, floor, ceiling or a window, for example, although that is an option if desired. The device 10 may be placed on a flat surface, such as a floor, table, desk, bookshelf, etc.

The one or more devices 10 in the home 12 in this example communicate with a security processing system 14 via a network 16. The network 16 may be the Internet, for example. The devices 10 may communicate with the network 16 wirelessly, such as by WiFi, or through the Ethernet, for example. The security processing system 14 may comprise a processing device 18 and a database 20, for example. The processing device 18 may comprise one or more computers or servers, for example. Multiple databases 20 may also be provided. The security processing system 14 may be a discrete entity connected to the network 16, or it may be a cloud-based system, for example. References to "cloud" or "cloud-based" system or network refer to a well-known distributed networks operated by cloud-based applications.

FIG. 1 also shows a primary user 22 with a user device 24 outside of the home 12 that can communicate wirelessly with the devices 10 and/or the security processing system 14 via the network 16, through WiFi and/or a cellular network, for example. Primary users 22 are users with complete access to the device 10 and the system 14. Primary users 22 have the ability to set preferences and customize the activities of the device 10 and/or the system 14. Household users are family members or other persons who reside in the house 12 or are otherwise associated with the location, such as an office, who interact with the device 10 and/or the system 14 on a regular, such as daily, basis. One important function of a primary user 22 is to receive information and notifications concerning the status of the home 12, as detected by the device 10, including notifications of potentially serious and life threatening situations, and respond to them, including instructing the device 10 and/or the system 14 how to react to the situation. In addition, the primary user 22 can teach the device 10 and/or the system 14 how to react to data detected by the device 10.

The primary user 22 may be near the home 12, at their place of business, or in any other location that can access the network 16. The user device 24 may be a mobile processing device, such as a smartphone or tablet, for example. The user device 24 may also be a desktop or laptop computer in the home 12 or outside of the home 12, such as an office. A user 22 may have multiple devices that can communicate with the devices 10.

FIG. 1 also shows a back up contact 26 with their own user device 24. A backup contact 26 has limited interaction with the system 14 when the primary user 22 does not respond to notifications provided by the system 14. Primary users 22 have an option to select or invite backup contacts during setup and at other times. The primary user 22 determines the circumstances when backup contacts receive notifications. In most instances when a primary user 22, or a household user, is unable to respond to a notification, a backup contact would be sent a notification and have the opportunity to resolve the incident. In one example, a backup contact that accepts the invitation would be redirected to a web portal to create an account. When a backup contact receives a notification by text or email, they are taken to a unique URL and presented with information about the event that triggered a notification and have the ability to respond to the event notification based on primary user preferences.

Multiple backup users can work together to resolve an incident. In one example, a primary user 22 may select up to three backup contacts and will also be able to change the roster of backup contacts from time to time when the need arises (for example when a primary user is on vacation with whomever they have designated as their first backup). Users will be able to toggle between which backup contact receives a notification first after an event has escalated based on numerical order, for example backup contact one would be the first backup contact to receive an escalated notification, and thereafter backup contact two would receive the notification if backup contact one has failed to resolve the event. The primary user 22 sets the escalation delay between contacts.

In addition, the devices 10, the security processing system 14, and/or the primary user 22 and the backup contacts 26, may communicate with first responders, such as the police 28, the fire department 30, and/or an ambulance service 32, for example, via the network 16. Alternatively, the devices 10, the processing system 14, and/or the user devices 24 may communicate with a call center 30, which may in turn communicate with the police 26, the fire department 28, the ambulance service 30 and/or the other parties described herein, via the network 16 or other networks, such as telephone networks. For example, the call center may send notifications to primary users 22 and backup contacts 26 via text, email, and/or phone call to their respective user device 24. The system 14 may also contact home or office emails addresses or phone numbers, for example.

If the primary user 22 does not respond to a notification concerning their home 12, for example, one or more backup contacts 26 may be contacted. If the backup contact or contacts 26 do not respond, then the system 14 may instruct the call center 34 to contact the police 28, fire department 30, and/or the ambulance 32 service, depending on the situation, or these parties may be contacted directly by the system 14. The system 14 or the call center 34 may then attempt to contact the primary user 22 to inform the user of the potential event and the actions taken.

Figure 2:
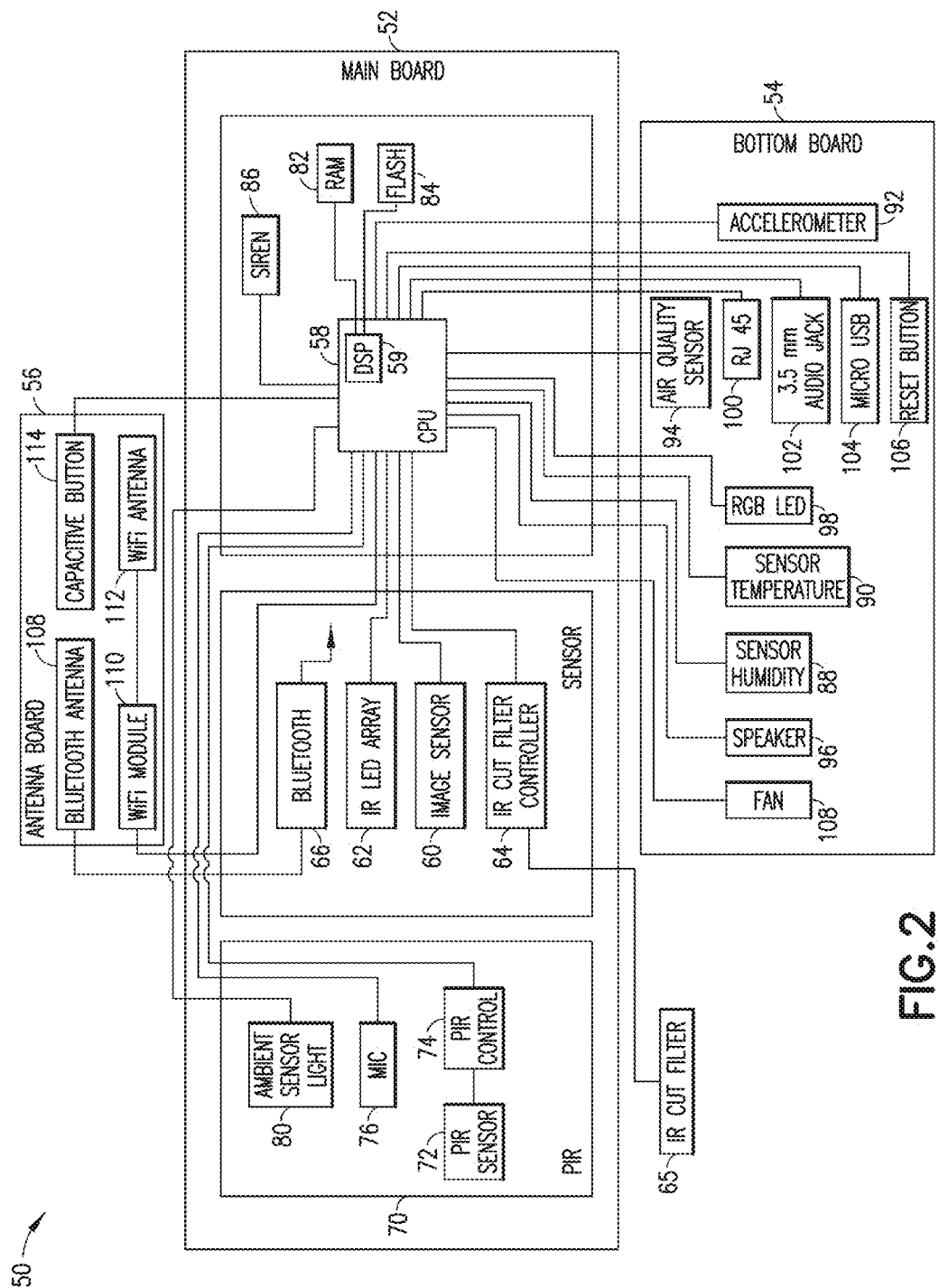
FIG. 2 is a block diagram of an example of a monitoring/security device in accordance with an embodiment of the invention.

FIG. 2 is a block diagram 50 of an example of a monitoring/security device 10 in accordance with an embodiment of the invention. In this example, the device 10 comprises a main printed circuit board ("PCB") 52, a bottom printed circuit board 54, and an antenna printed circuit board 56. A processing device 58, such as a central processing unit ("CPU"), is mounted to the main PCB 52. The processing device may include a digital signal processor ("DSP") 59. The CPU 58 may be an Ambarella digital signal processor, A5x, available from Ambarella, Inc., Santa Clara, Calif., for example.

An image sensor 60 of a camera, an infrared light emitting diode ("IR LED") array 62, an IR cut filter control mechanism 64 (for an IR cut filter 65), and a Bluetooth chip 66 are mounted to a sensor portion 68 of the main board 52, and provide input to and/or receive input from the processing device 58. The main board 52 also includes a passive IR ("PIR") portion 70. Mounted to the passive IR portion 70 are PIR sensor 72, a PIR controller, such as a microcontroller, 74, a microphone 76, and an ambient light sensor 80. Memory, such as random access memory ("RAM") 82 and flash memory 84 may also be mounted to the main board 52. A siren 86 may also be mounted to the main board 52.

A humidity sensor 88, a temperature sensor 90 (which may comprise a combined humidity/temperature sensor, as discussed below), an accelerometer 92, and an air quality sensor 94, are mounted to the bottom board 54. A speaker 96, a red/green/blue ("RGB") LED 98, an RJ45 or other such Ethernet port 100, a 3.5 mm audio jack 102, a micro USB port 104, and a reset button 106 are also mounted to the bottom board 54. A fan 108 may optionally be provided.

A Bluetooth antenna 108, a WiFi module 110, a WiFi antenna 112, and a capacitive button 114 are mounted to the antenna board 56.

The components may be mounted to different boards. For example, the Wifi module 110 may be mounted to the main board 52, as shown in the Figures discussed below.

Figure 3:
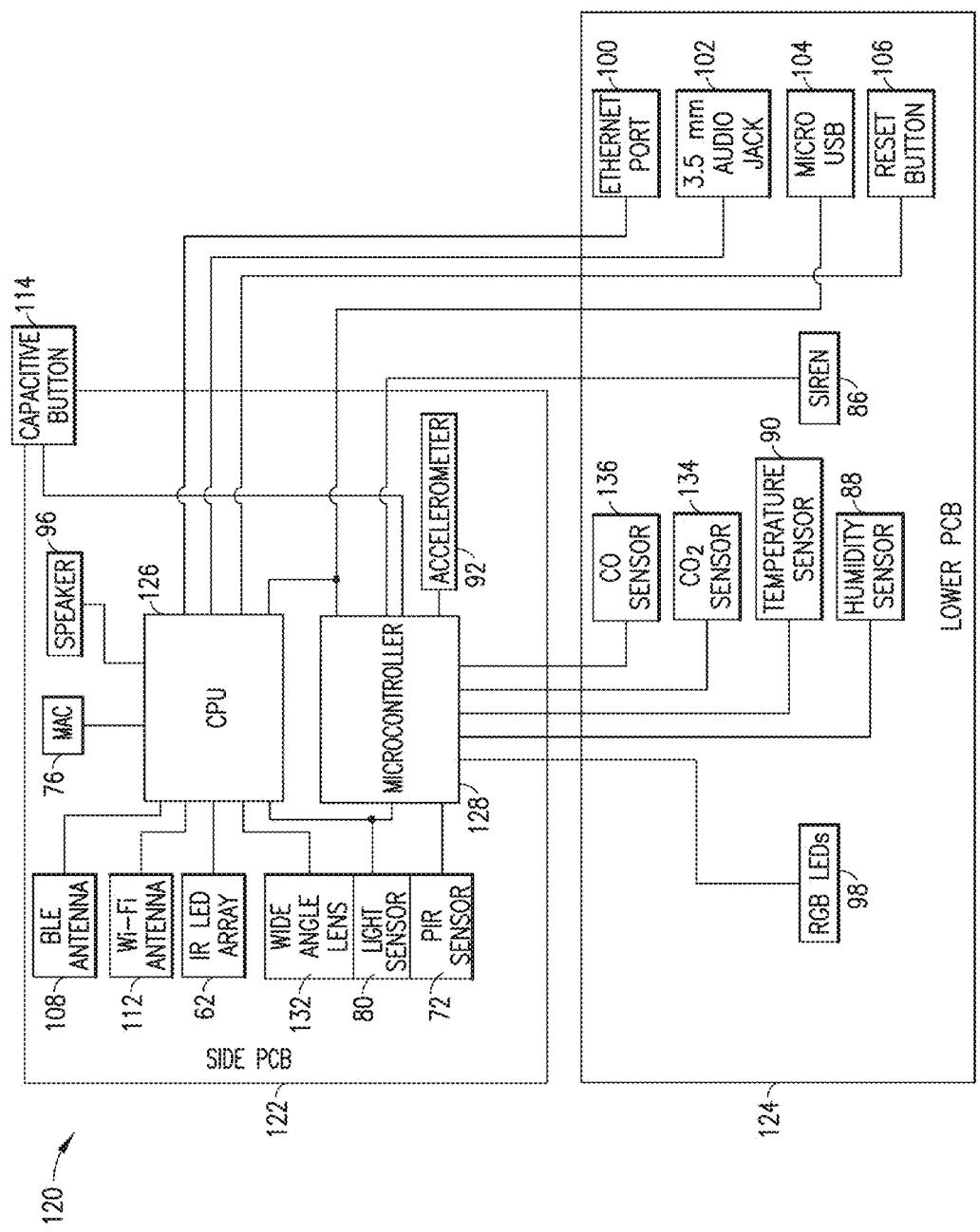
FIG. 3 is a block diagram of another example of the device of FIG. 1.

FIG. 3 is a block diagram 120 of another example of the device 10, comprising two printed circuit boards, a side PCB 122, and a lower PCB 124. Components common to FIGS. 2 and 3A are commonly numbered. In this example a CPU 126 and a microcontroller are mounted to the side PCB 122, along with the Bluetooth low energy ("BLE") antenna 108, the Wifi antenna 112, the IR LED array 62, a wide angle lens 132, the ambient light sensor 80, the PIR sensor 72, the accelerometer 92, the capacitive switch 114, the microphone 76 and the speaker 96. The RGB LEDs 98, the humidity sensor 88, the temperature sensor 90, a carbon dioxide ($CO_2$) sensor 134, a carbon monoxide sensor 136, the siren 86, the Ethernet port 100, the audio jack 102, the micro USB port 104, and a reset button 106 are provided on the lower PCB 124.

Figure 4:
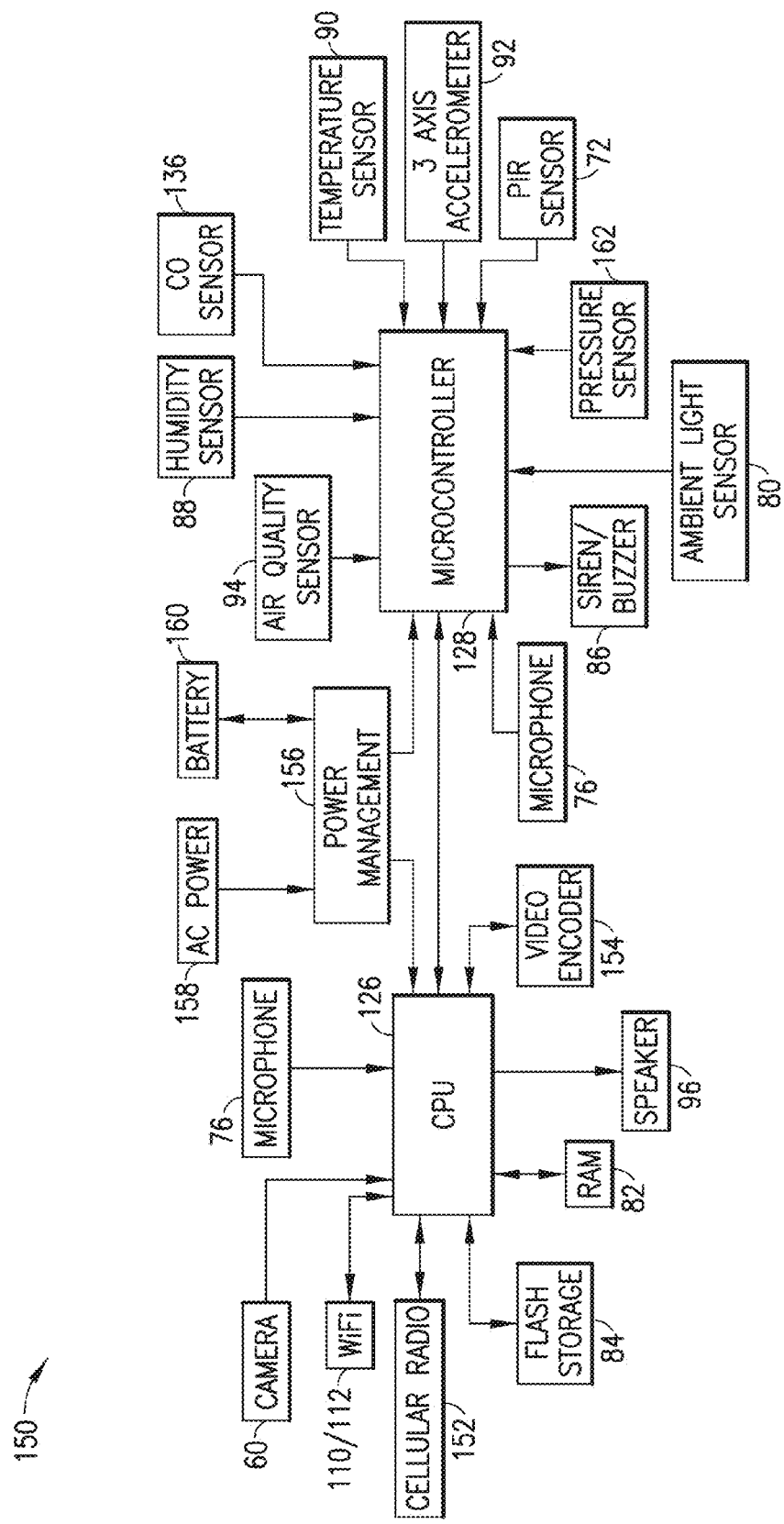
FIG. 4 is another example of a block diagram of the device of FIG. 1.

FIG. 4 is another example 150 of a block diagram of the device 10. Components common to FIGS. 2 and 3 are commonly numbered and not further discussed. FIG. 4 further shows a cellular radio 152, and a video encoder 154 connected to the CPU 126. A power management chip 156 is connected to both the CPU 126 and the microcontroller 128. AC power 158 and a battery 160 are connected to the power management chip. A pressure sensor 162 is connected to a microcontroller 164.

Figure 5:
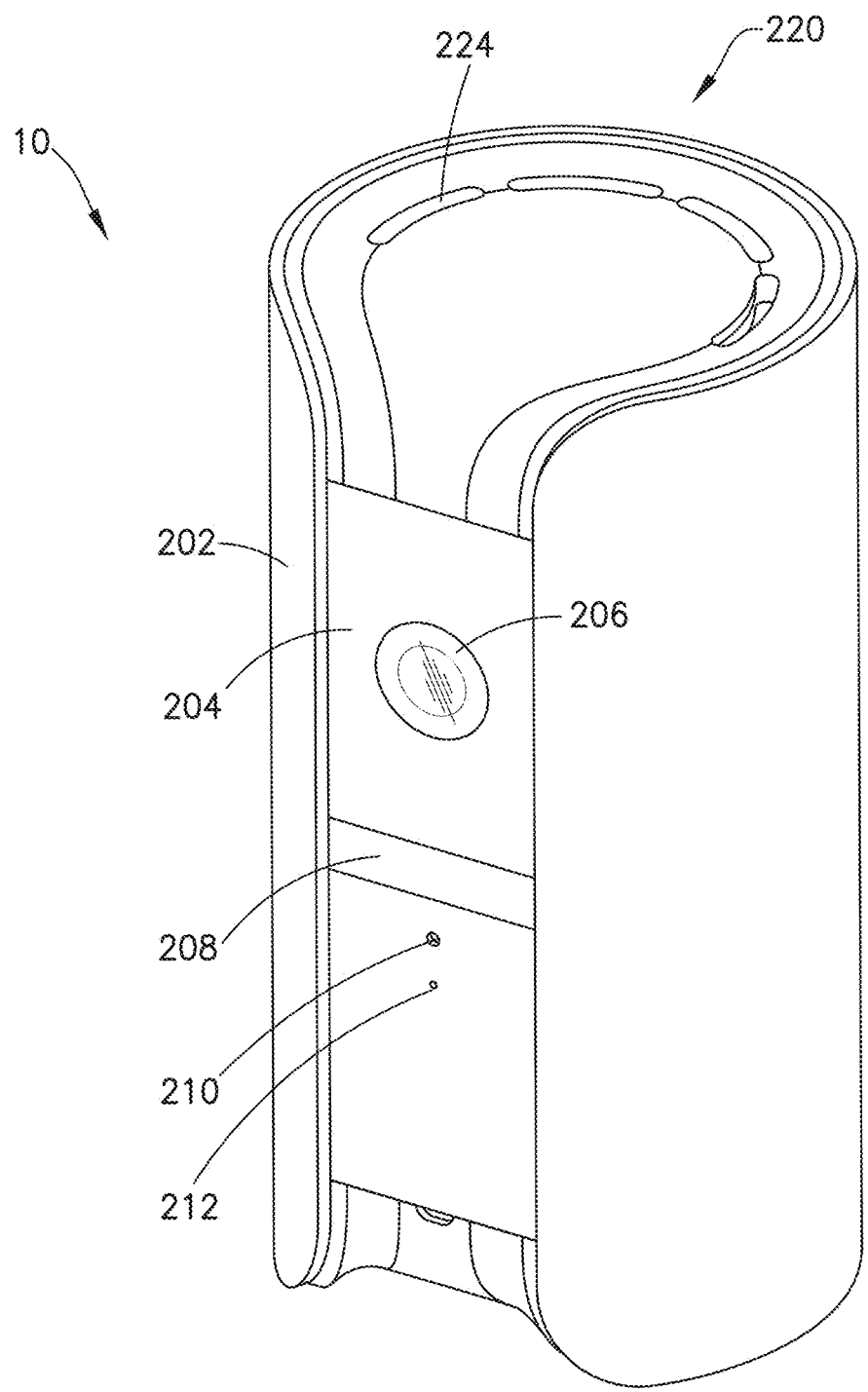
FIG. 5 is a perspective view of a monitoring/security device in accordance with an embodiment of the invention.

FIG. 5 is a perspective view of a monitoring/security device 10, in accordance with an embodiment of the invention. The device 10 comprises an outer housing 202 and a front plate 204. In this example, the plate 204 includes a first window 206, which is in front of the image sensor 60. A second window 208, which is rectangular in this example, is in front of the infrared LED array 62. An opening 210 is in front of the ambient light detector 80, and an opening 212 is in front of the microphone 76. The front plate 204 may comprise black acrylic plastic, for example. The black plastic acrylic plate 204 in this example is transparent to near IR greater than 800 nm.

Figure 6:
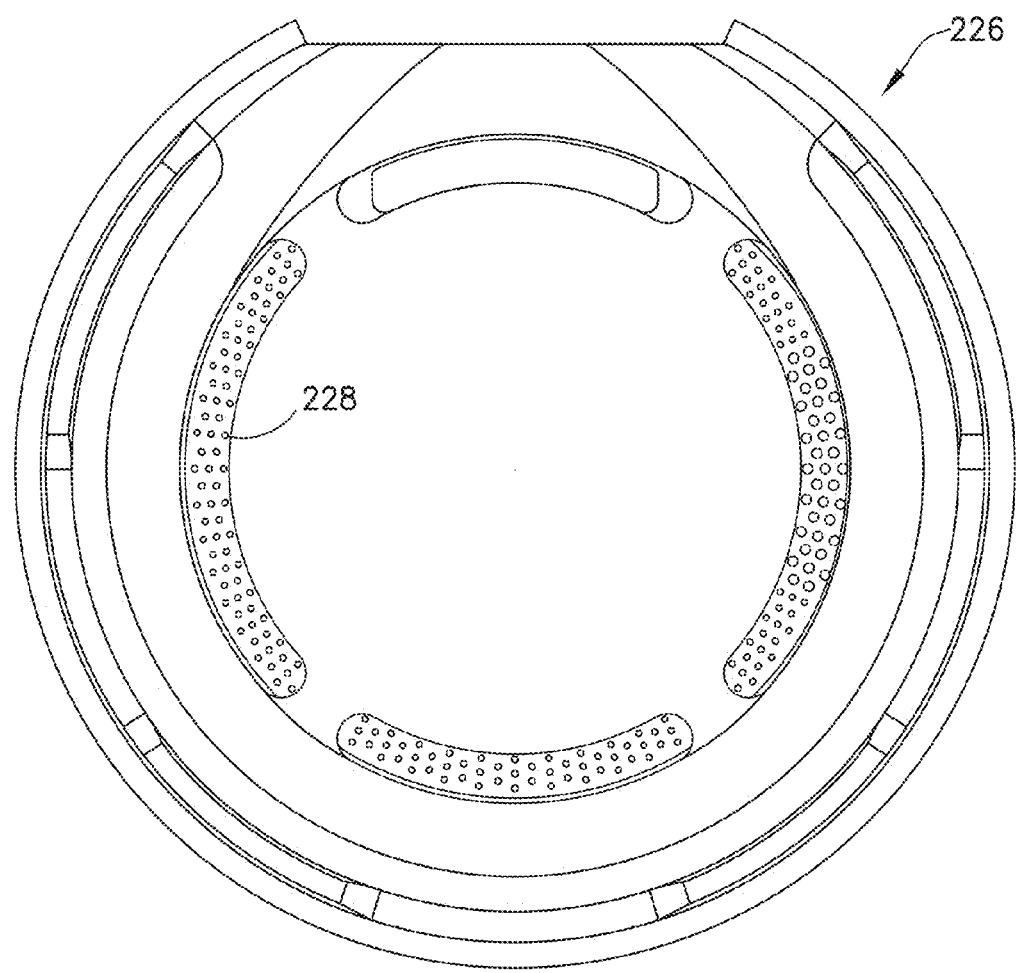
FIG. 6 is a bottom view of the device, in accordance with the embodiment of FIG. 5.

The top 220 of the device 10 is also shown. The top 220 includes outlet vents 224 through the top to allow for air flow out of the device 10. FIG. 6 is a bottom view of the device 10, which shows the bottom 226 and inlet vents 228 to allow air flow into the device 10. The top 220 and the bottom 226 of the device 10 may be separate, plastic pieces that are attached to the housing 202 or an internal housing during assembly, for example. Air passing through the bottom, inlet vents 228 travel through the device 10, where it picks up heat from the internal components of the device, and exits through the top, outlet vents 228. In this example hot air rises through the device 10 by convection, causing air to be drawn into the device from the bottom vents 226 and exit through the top vents 220. A fan 108 (FIG. 2, for example), may be provided to draw external air into the device 10 through the bottom, inlet vents 228 and drive the air out of the device through the top, outlet vents 224, as well.

The size of the vents 224 have to be large enough to allow heat to flow out of the unit and not convect into the device 10, but the vents cannot be so large that a child can stick a finger into the unit. Alternatively, a larger vent is made and the vent is covered with a Gore-Tex or nylon mesh to prevent water ingress but allow air to exit the unit.

Figure 7:
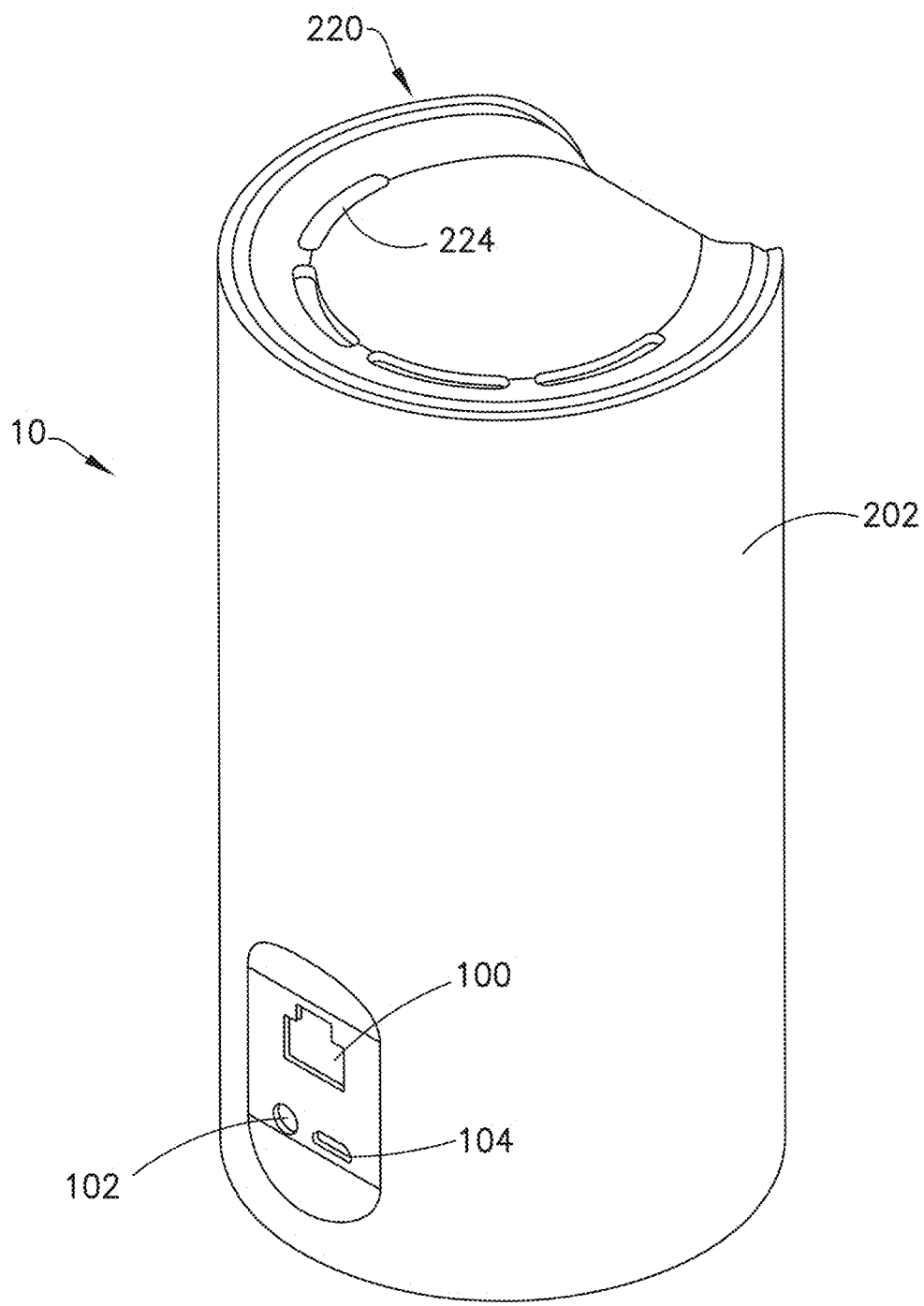
FIG. 7 is a rear perspective view of the device, in accordance with the embodiment of FIG. 5.

FIG. 7 is a rear perspective view of the device 10, showing the Ethernet connector 100, the audio jack 102, and a USB port 104.

Figure 8:
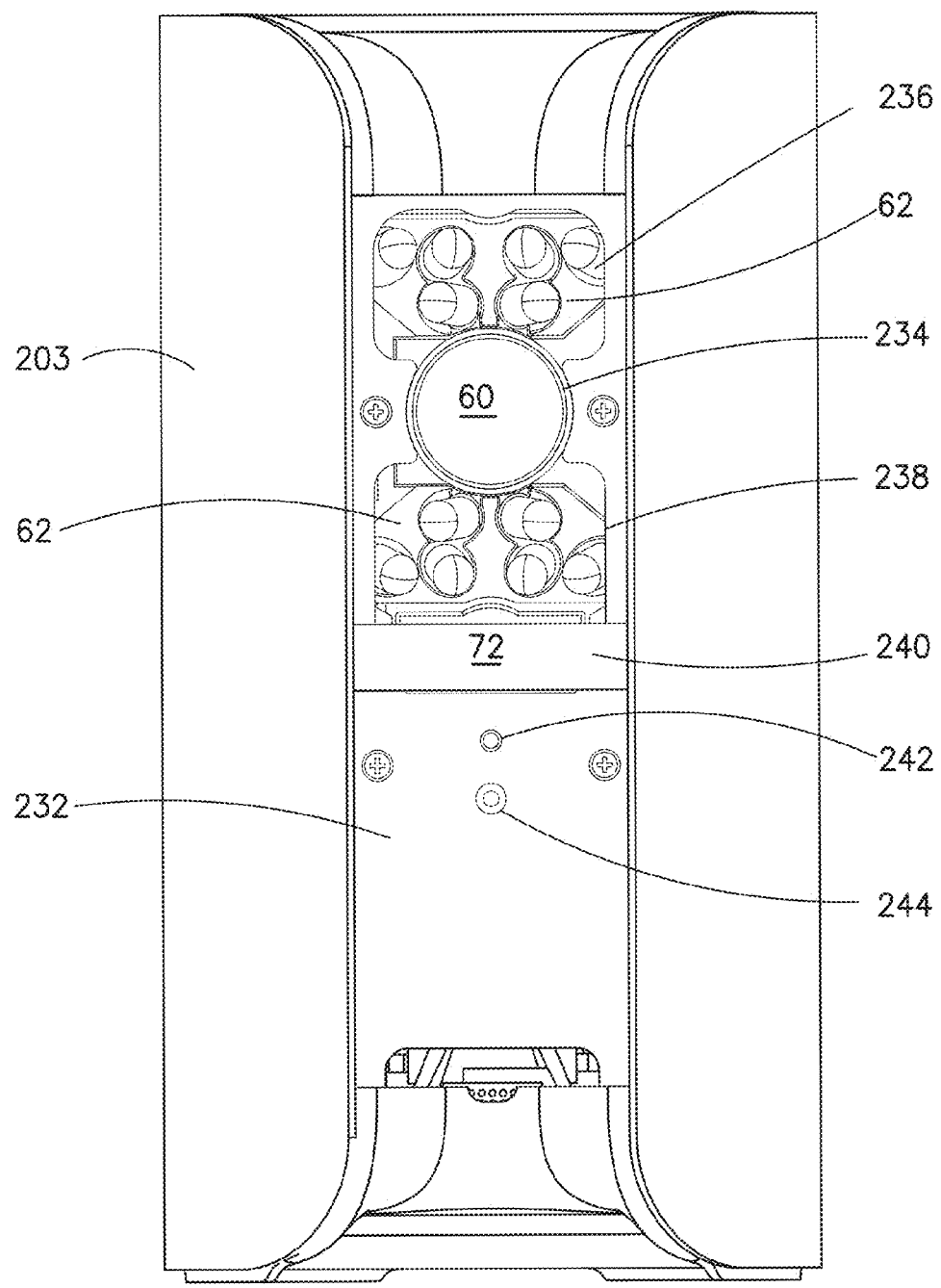
FIG. 8 is a front view of the device, in accordance with the embodiment of FIG. 5.

FIG. 8 is a front view of the device 10 with the front plate 204. A front wall 232 that connects the opposing curved edges of the curved housing to each other is shown. The front wall 232 defines an opening having a first, partially circular section 234, an upper rectangular section 236 above the partially circular opening and a second, lower rectangular section 238 below the partially circular section. A smaller rectangular open section 240 is below the second rectangular section 238.

The image sensor 60 is behind the partially circular section 234, the IR LED arrays 62 are behind the first and second rectangular sections 236, 238 and the passive IR sensor 72 is behind the smaller, lower rectangular section 240. The partially circular section is behind the first window 206 in the plate 204. The smaller rectangular section 240 is behind the rectangular window 208 in the plate 204. Additional openings 242 and 244 are provided behind the openings 210, 212 in the plate 204, in front of the ambient light sensor 80 and the microphone 76. It is noted that while some of the IR LEDs 62 behind the rectangular sections 236, 238 are partially obscured by the front housing, the LEDs are angled, so that the infrared light emitted by the LEDs are directed out of the device 10.

Figure 9:
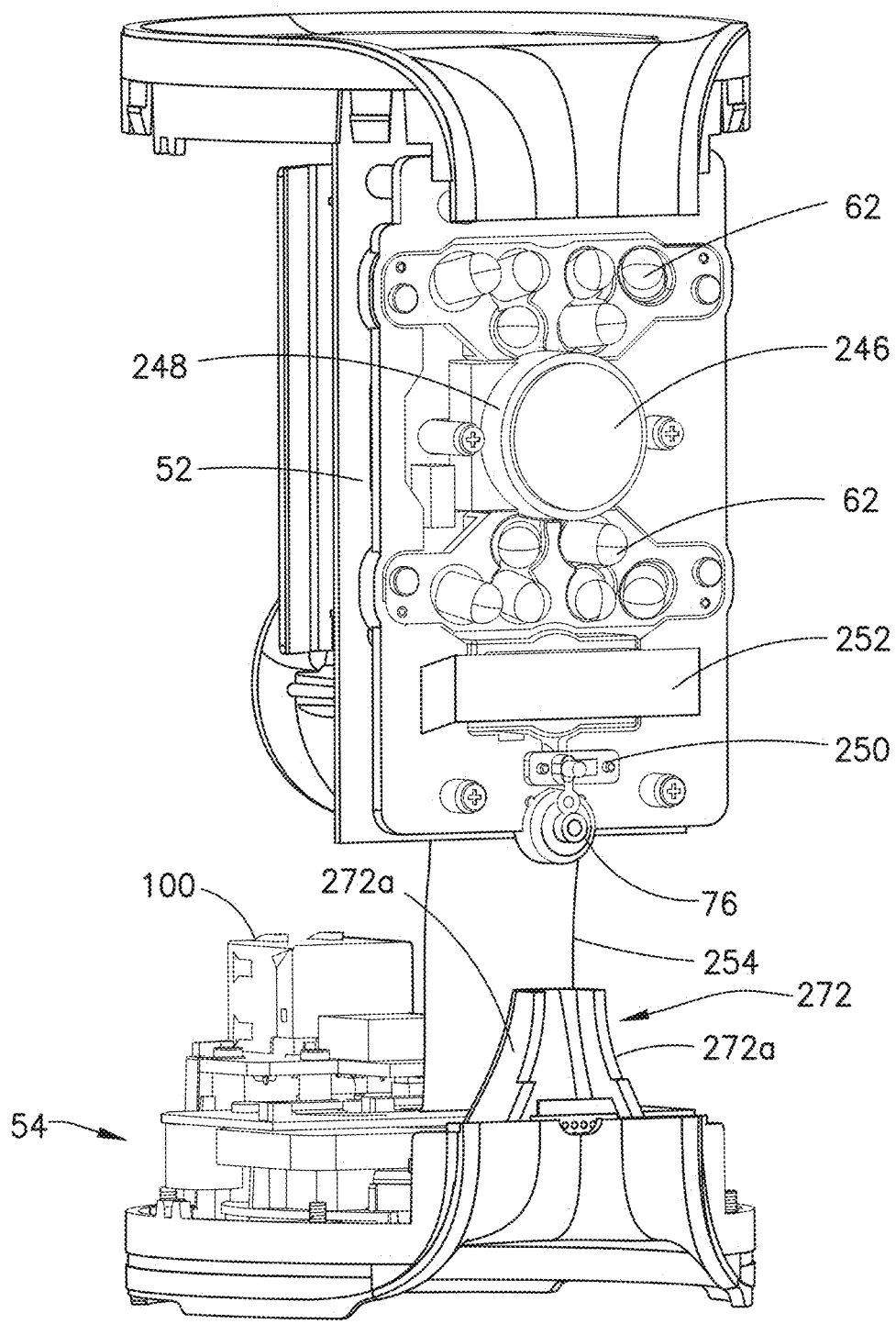
FIG. 9 is a front perspective view of the main board of the device, in accordance with the embodiment of FIG. 5.

FIG. 9 is a front perspective view main board 52. Camera optics 246 are shown in front of the imaging sensor 60 (not shown). The camera optics are supported within a barrel 248. A light pipe 250 is in front of the ambient light sensor 80, to couple the sensor to the opening 242 in FIG. 8. The microphone 76 is below the light pipe 250. Also shown is a rectangular lens 252 in front of the PIR sensor 72. The lens 252 and the sensor 72 are discussed further below.

A portion of the bottom board 54 is shown. A flexible printed circuit ("FPC") 254 connects the main board 52 to the bottom board 54. The rear of the Ethernet port 100 is also shown. Other components shown in FIG. 9 are discussed further below.

Figure 10:
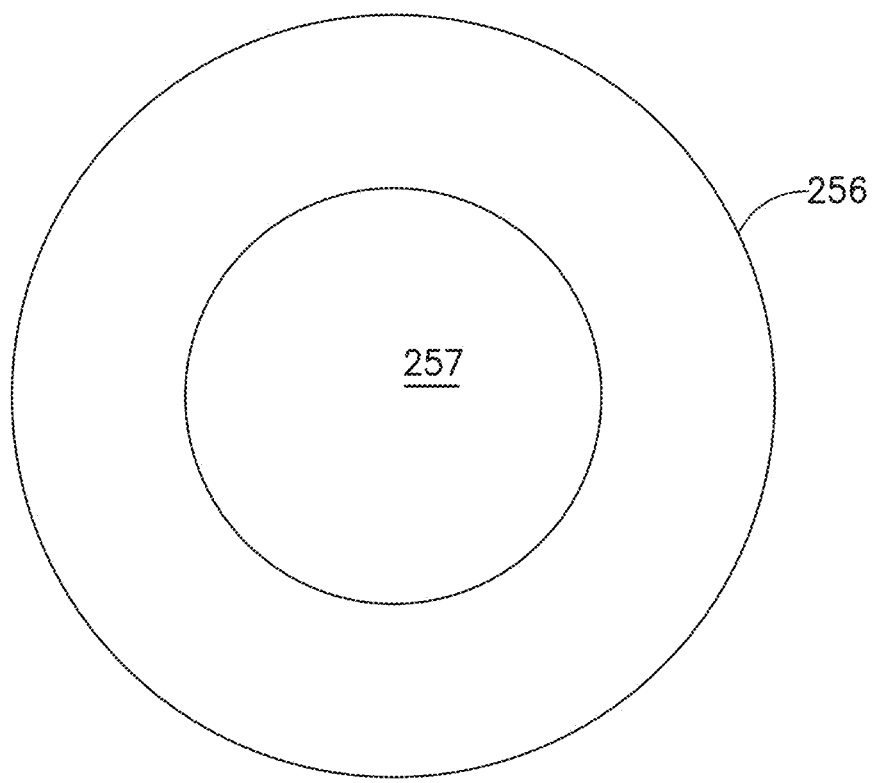
FIG. 10 is a front view of a disk that may be provided in front of the camera optics in the device, in accordance with the embodiment of FIG. 5.

FIG. 10 is a front view of a disk 256 with an opening 257 that may be provided in front of the optics 246. The disk 256 is painted black to blend in with the black front plate 204, thereby making the imaging sensor 60 and camera optics 246 less noticeable during use in a home 12, for example. The disk 256 may be plastic, for example.

Figure 11:
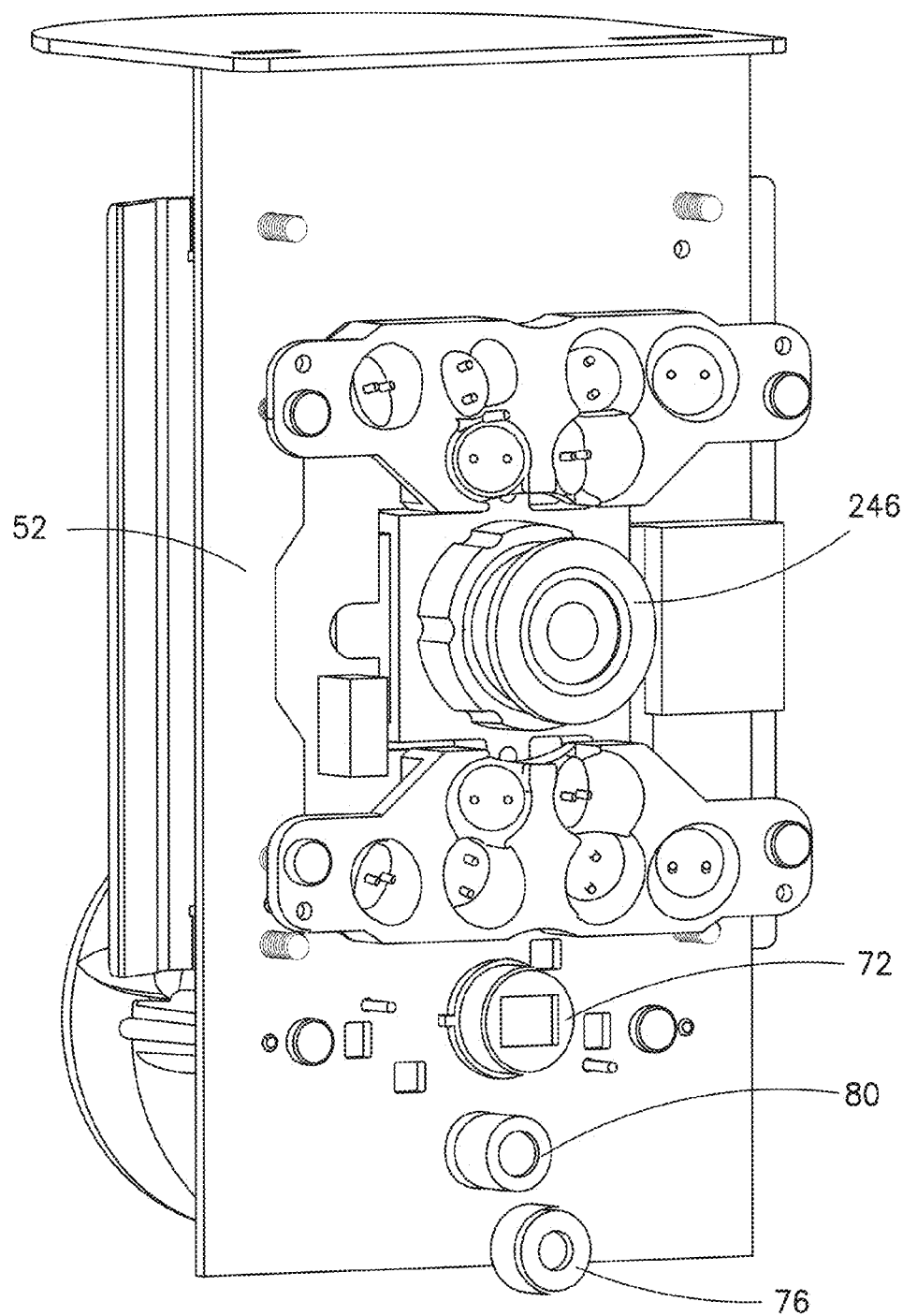
FIG. 11 is a perspective view of the main board with a PR lens removed, in accordance with the embodiment of FIG. 5.

FIG. 11 is a perspective view of the main board 52 with the PIR lens 252 removed to show the PIR 72 mounted to the main PCB. A light pipe in front of the ambient light sensor is also removed, to show the light sensor mounted to the main board 54. The barrel 248 is also removed, to better show the camera optics 246.

Figure 12:
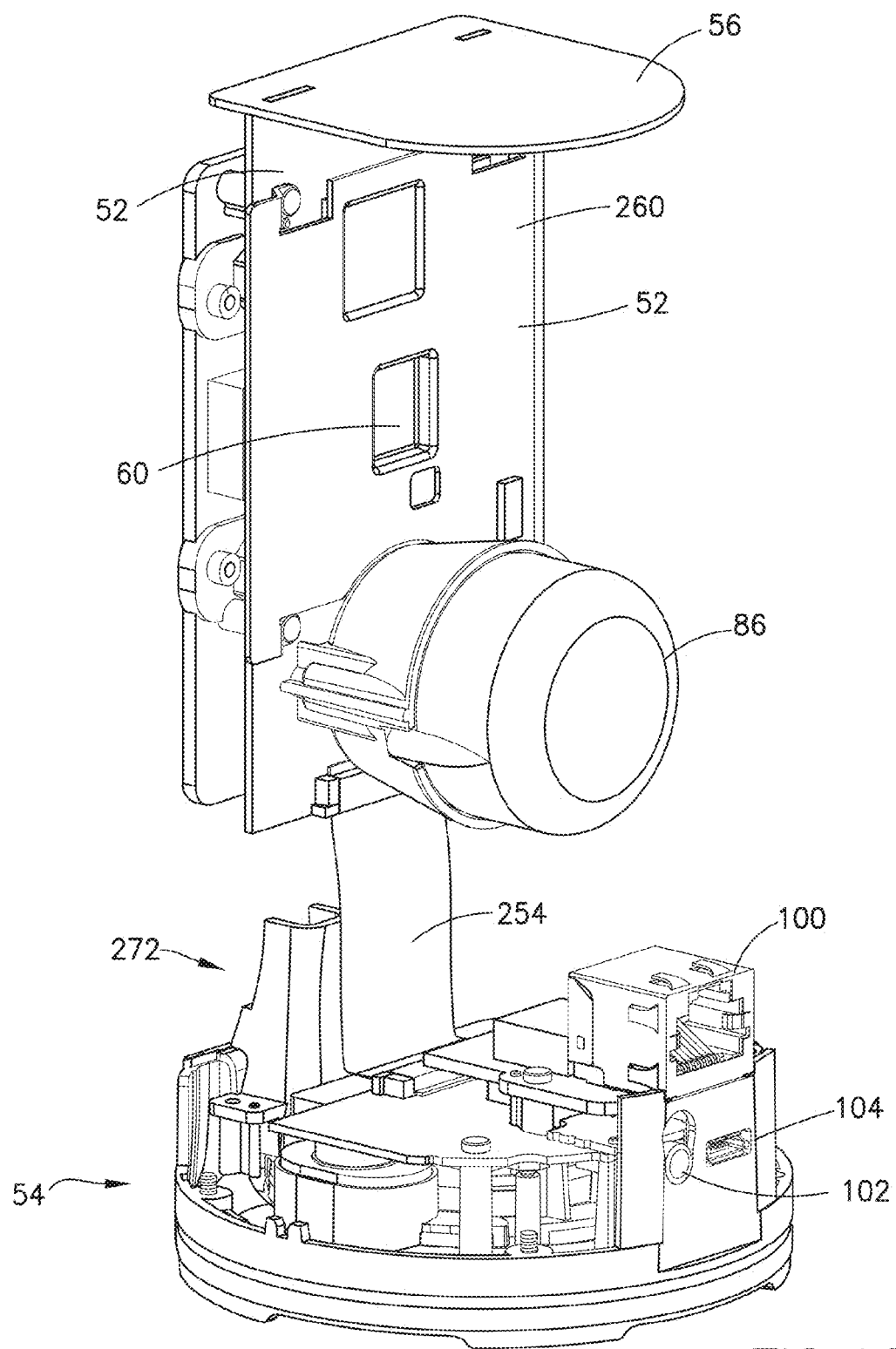
FIG. 12 is a rear perspective view of the main board, the bottom board, and the antenna board, in accordance with the embodiment of FIG. 5.

FIG. 12 is a rear perspective view of the main board 52, the bottom board 54, and the antenna board 56. A heat sink 260 is applied to the back surface of the main board 52. The siren 86 mounted to the rear surface of the main board 52. Air flow through the bottom vents 228, past the heat sink 260, removes heat from the heat sink, prior to exiting the device 10 through the top vents 224. The imaging sensor 60 is also shown. FIG. 12 also shows the Ethernet port 100, the audio jack 102, and the USB power port 104. The audio jack 102 maybe a 3.5 mm barrel jack, for example.

Figure 13:
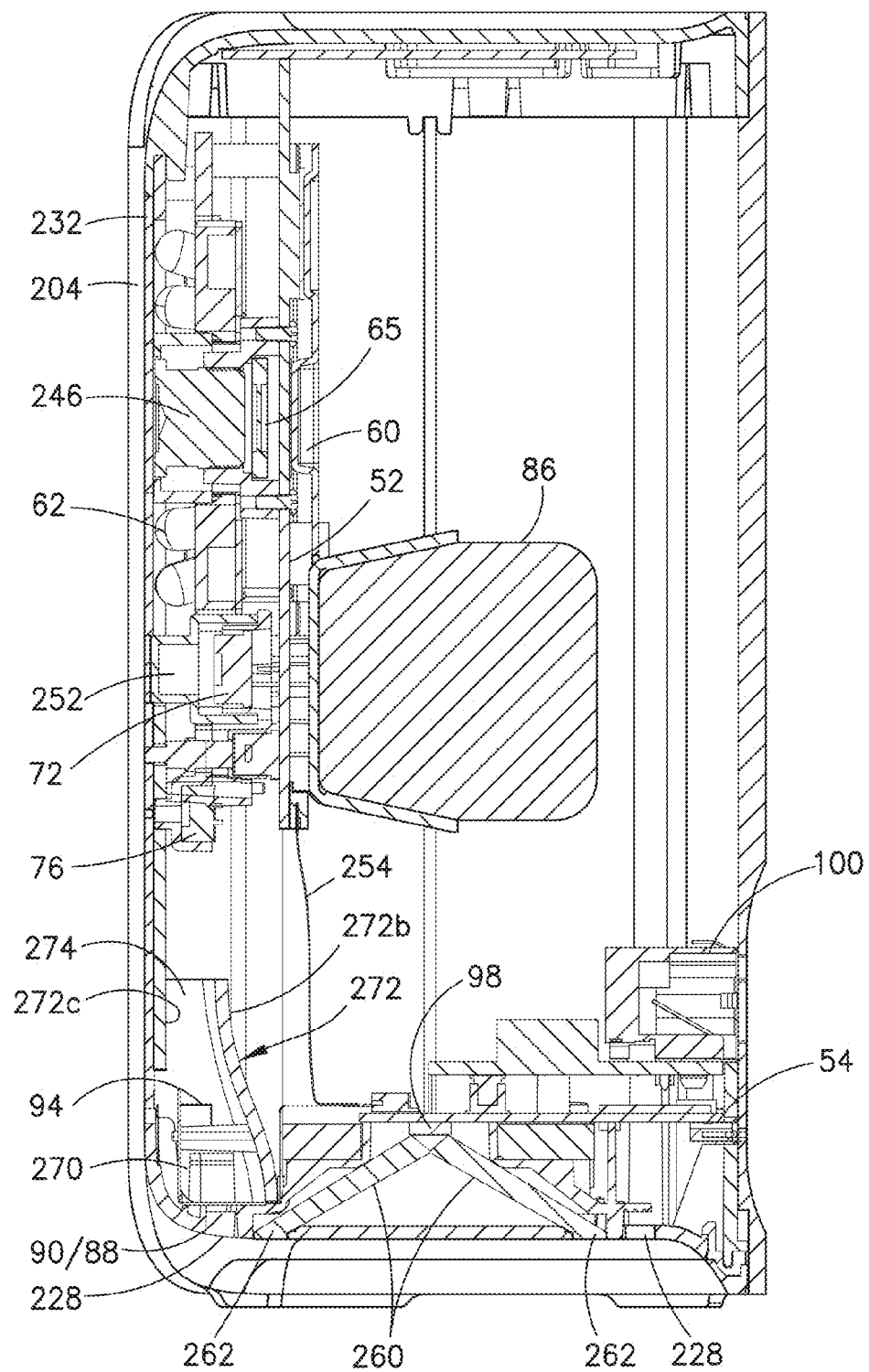
FIG. 13 is a cross-sectional view of the device, in accordance with the embodiment of FIG. 5.

FIG. 13 is a cross-sectional view of the device 10. The front plate 232 and the position of the front housing 204 are shown. Also shown in this view is an RGB LED 98 mounted to the bottom board 54. Below the RGB LED is a cone shaped light guide 260 (shown in cross section in this view) diverging from the LED. The circular bottom 262 of the light guide 260 provides colored illumination indicative of the state of the device, such as armed or disarmed, for example, out the bottom of the device 10.

FIG. 13 also shows the temperature/humidity ("T/H") sensor 90/88 and the air quality sensor 94 mounted to a FPC 270, which is mounted bottom board 54 in this example. The T/H sensor 90/88 is proximate one of the bottom vents 228, so that external air from the location where the device 10 is located passes over the sensor. An air guide 272 is provided around the T/H sensor 90/88, the air quality sensor 94, and one of the bottom vents 226. The air guide 272 guides external air received through the bottom vent past the sensors, and insulates the sensors from the heat generated within the device 10, as described further below.

The air guide 272 in the example comprises side walls 272a, and a rear wall 272b, as shown in FIGS. 9 and 13, for example. The front 272c of the air guide 272 is provided by the inner surface of the housing 202. The rear walls and the sidewalls taper inwardly toward the front of the device so that the bottom entrance to the guide 272 is larger than the exit 274. It has been found that the taper improves the accuracy of the temperature detected by the T/H sensor 90/88. The air guide 272 may comprise acrylic plastic, for example, as discussed further below.

The housing 202 may comprise anodized aluminum, which provides a high quality appearance and high durability. Since the anodized aluminum may act as an electrical insulator, the inside surfaces of the housing 202 may be polished or masked during anodizing to allow the electrical ground to be tied to the aluminum metal housing. This provides a large sink for electrostatic discharge (ESD) and a partial shield against the electromagnetic radiation from the device 10 and electromagnetic susceptibility from external sources. The polished inside surfaces of the housing 202 reduce the thermal emissivity and enable thermal radiation to escape the unit better and thereby thermally isolate the environmental sensors better.

The image sensor 60 of the camera may comprise a CMOS, CCD image array sensor, which is used as the transducer to digitally capture, transmit and store images or video. The sensor may have a large pixel size to increase the light gathering capability. Back side illuminated sensors may be used to further enhance the dynamic range in low light conditions.

In this example, the imaging sensor 60 is sensitive to visible light and also near IR (between 700 nm and 1100 nm wavelengths), which enables the sensor to capture "night" vision images. The image sensor 60 can be either electronic rolling or global shutter and can achieve at least 30 fps of video at 720p and 1080p resolutions, and can produce larger resolution still images than 1080p for greater detail, pixel binning, long exposures, and high dynamic range imaging ("HDR") techniques may be used to enhance dynamic range, which helps create accurate and high quality images at low light levels. The image sensor may be an Aptina AR330, available from Aptina Imaging Corporation, San Jose, Calif., for example.

The camera optics 246 may comprise a fixed focus, wide angle multi-element lens to capture visual information about the location. In this example, the angle is 140 degrees. The lens may be optimized for spatial resolution and chromatic aberration. The lens mounts to the image sensor 60 through a screw mount to ensure precise focus during mass production. The lens may be made of high quality glass such as BK7 or Sapphire, for example, to ensure high image quality.

The imaging optics 246 are protected from the environment using a flat exit window that is made of chemical strengthened or naturally strong glass, such as Gorilla Glass or Sapphire glass, for example. The exit window may be covered with an anti-reflective coating, oleophobic coating to prevent finger prints and smudges. The exit window may also have a hydrophobic coating to prevent water droplets or condensation from accumulating that might occlude the pictures or video. The window 206 in the black front acrylic plate 204 accommodates the FOV of the sensor 60 and the optics 246.

A 3-axis or 6-axis accelerator 92 (FIGS. 2, 4), may be provided placed on the bottom board 54 of the device or in another location to detect motion of the device 10, itself, such as the device being knocked over, for example.

Heat generated by components within the device 10, such as the processing device 58, the image sensor 60, and the Wifi module 110, may adversely influence the ambient temperature and humidity measurements by the T/H sensor 90/88. Since heat transfer occurs through conduction, convection, and radiation, embodiments of the invention seek to decrease the effects of these heat transfer modes on the T/H sensor 90/88.

The air guide 272, discussed above, defines a thermal barrier for the T/H sensor 90/88 and the air quality sensor 94, to isolate them from both conduction and radiation. By mounting the T/H and air quality sensors to the FPC 270, these sensors are isolated from heat transfer through conduction from. In addition, very thin traces are used on the FPC. The FPC may comprise polyamide, which has a high thermal resistance and decreases heat transfer that might have occurred if the T/H sensor and air sensor were mounted directly to the bottom board 54. Other sensors may be positioned within the air guide 272 for thermal isolation, as well In this example, the air guide 272 comprises plastic acrylic wrapped in high thermal reflectivity material, such as polished copper or Mylar, for example. Since the anodized aluminum of the housing has a high thermal wavelength emissivity, polishing the inside walls of the housing 202 reduces thermal radiation.

In addition, the main heat generators such as the processing device 58 and the Wifi module 110, which are mounted to the main board 52 in this example, are heat "sunk" using a high conductivity material as a heat sink 260, as shown in FIG. 12. The heat device thermally coupled to the polished inner walls of the aluminum walls.

The air quality sensor 94 may be a volatile organic compound ("VOC") sensor, as in shown in the art.

A thermistor (not shown) may be provided on the main board and/or the antenna board, for example, to measure the heat generated by the heat generating components, which may be used to correct the temperature detected by the T/H sensor 90/88, if necessary.

Figure 14:
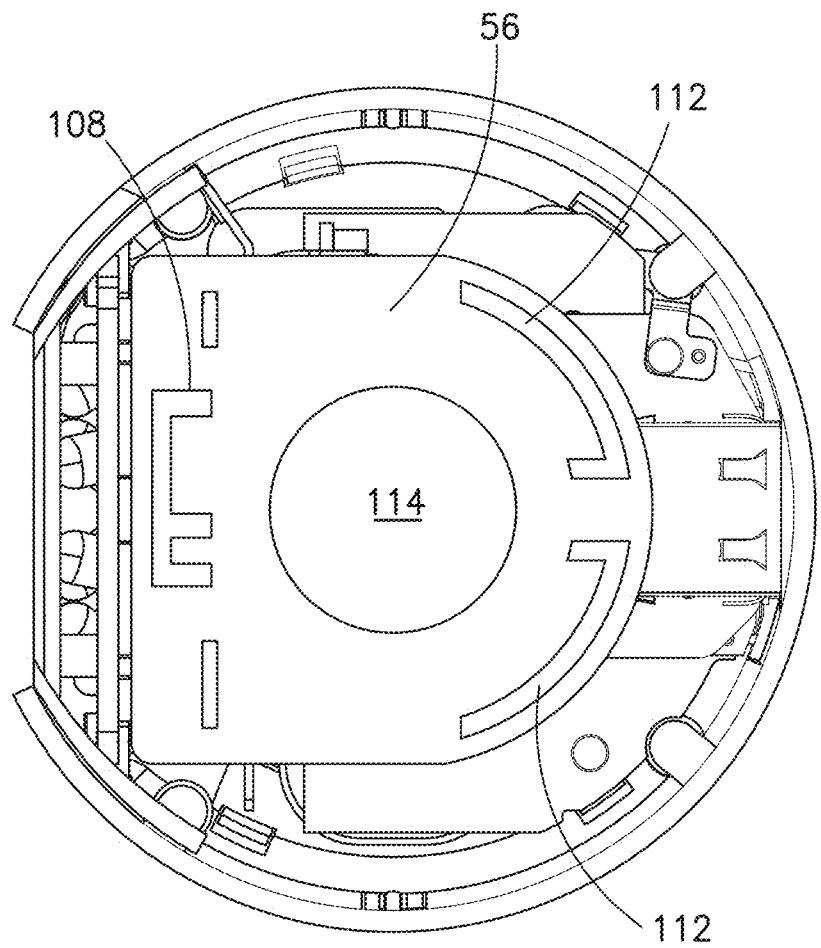
FIG. 14 is a top view of the antenna board, showing a Bluetooth antenna, a WiFi antenna, and a capacitive switch, in accordance with the embodiment of FIG. 5.

FIG. 14 is a top view of the antenna board 56, showing the Bluetooth antenna 108, the WiFi antenna 112, and the capacitive switch 114. In this example, the Bluetooth antenna 108 and the WiFi antenna 112 defined by the antenna board 54, as opposed to being sheet metal based, and are placed under the top surface of the top 220 of the device 10. This ensures that the RF energy does not get attenuated by the metal housing 202, which is electrically grounded. Alternatively, metal antennas may be integrated into the top metal cap or the main metal housing. Alternatively, the top 220 may be made of plastic or metal with plastic pattern inserts or overmolds to define the antenna. A metal top 220 can also act as a heat radiator to keep the inside of the device 10 cool.

The capacitive switch 114 may be used to change modes of the device 10 and the system 14, as discussed below.

Night and dark vision operation is enhanced by illuminating the location with near IR light by the IR LED arrays 62. The near IR LED arrays may emit radiation in the range of 850-875 nm, for example. 850 nm-875 nm light is very weakly visible to mostly invisible to most humans. However, since the CMOS image sensor 60 is sensitive to this wavelength band, it can respond to these illumination sources by providing well illuminated images, even when the room where the device is located is dark. It may be determined whether it is nighttime based on the light detected by the ambient light sensor 80, for example.

The IR LED arrays 62 around the image sensor comprise near IR LEDs, (typically 850-880 nm to illuminate the surroundings in night vision mode, without blinding or distracting or being visible to the user at night. The IR LED arrays 62 provide uniform illumination in the field of view ("FOV") of the camera. The IR LEDs are placed behind a black acrylic window to remain invisible to the user. The black acrylic window allows only near IR to pass through. Most 850 nm LEDs are partially visible to the human eye because of a wide transmission bandwidth that extends down towards the visible spectrum. To avoid this distraction to the user, a band pass or high pass filter may be provided on the inside of the front housing (black acrylic sheet) to block any visible light from passing through the window.

Figure 15:
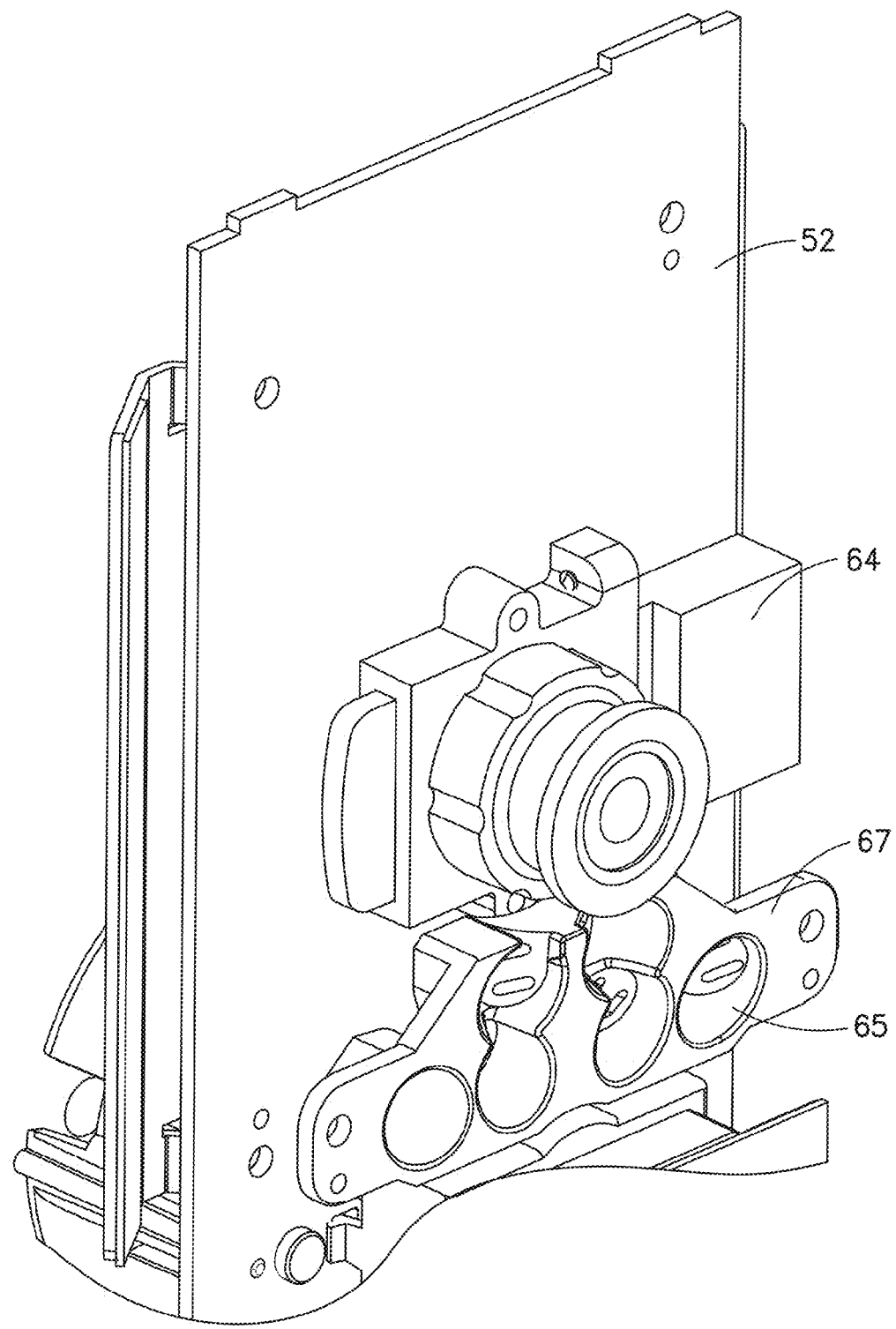
FIG. 15 is a view of the main board, showing an actuator for an IR filter, in accordance with the embodiment of FIG. 5.

A near IR filter 65 is provided to block near IR ("NIR") radiation above 700-750 nm, for example, to enhance spatial resolution and other image quality parameters on a CMOS image sensor 60 during daytime, as shown in FIG. 13 and FIG. 15. It need not be used at night. Movement of the filter 60 may be provided by an actuator 64, as shown in FIG. 15. The actuator 64 may be an electro-optic system, such as is used in LCS shutters, or an electro-mechanical system, such as is used in electromechanical shutters. Operation of the near IR filter actuator 64 may be controlled by the processing device 58, for example, as shown in FIG. 2. FIG. 15 also shows cavities 65 in a supporting structure 67 for respective LEDs in the array 62.

Figure 16:
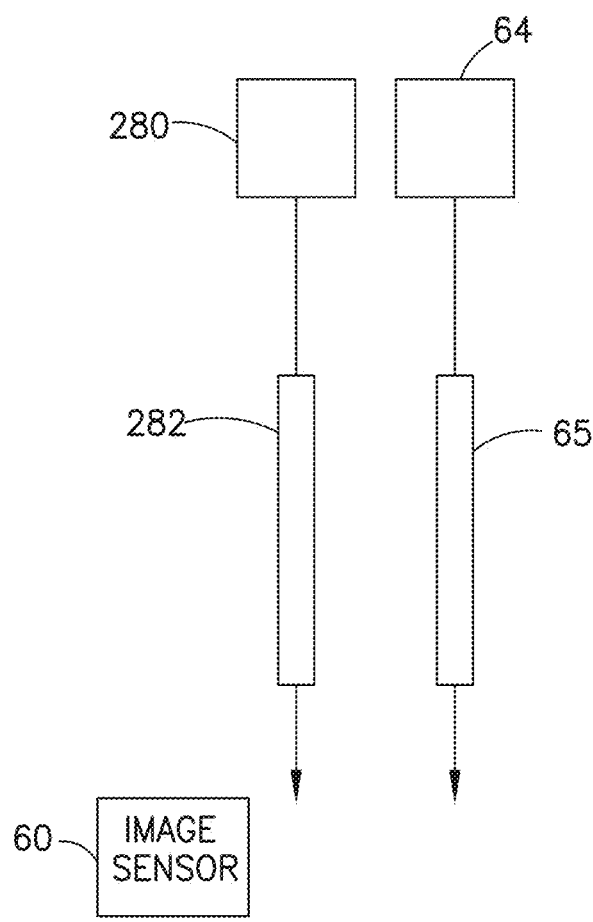
FIG. 16 is a schematic representation of two IR filters for selective placement in front of an imaging sensor, in accordance with an embodiment of the invention.

In accordance with another embodiment of the invention, a second, independent IR filter 282, under the control of another actuator 280 or the same actuator 64 that controls operation of the cut filter 65, may be provided, as shown schematically in FIG. 16. The second filter 282 acts as a narrow band pass filter to allow only a narrow wavelength of light to pass through. For example, the second IR filter could be 850 nm band pass filter with a 30 nm band width. This filter 282 can therefore be used for 3D time of flight, structured light based 3D cameras. The actuator 280 may also be controlled by the processing device 58, for example.

In an example of a 3D imaging system that may be used in accordance with an embodiment of the invention, the illumination source may be the near IR LED arrays (850 or 875 nm) that would be pulsed at very high frequencies (>10 MHz) using a standard pulse width modulation ("PWM") circuit. The received "pulsed" or continuous wave images are provided to the processing device 58 or another processing device to compute depth of an image, for example. To obtain the flight data that could be used to device 3D information, the LEDs in the array 62 may be pulsed. The time for infrared light to be detected by the image sensor 60 after emission for an LED pulse may be measured by the processing device 58. Infrared light will return from objects further away, after the infrared light returns from objects closer to the device 10. 3D information may be used to determine a precise location of a fire, an intruder, for example. It could also be sued to obtain in at least partial 3D image of a person, which would assist in the identification of the person based on the volume of the person, a can used in conjunction with video data from the image sensor. The processing of video data is discussed below. The first filter would not be activated while the second filter is activated.

The functions of the processing device 58 include running the operating system and embedded software that runs on the operating system, to exercise the various hardware on the device 10 appropriately, and compressing the incoming raw video signal from the image sensor to a high quality compact stream that can be efficiently transmitted over the Internet, as discussed further below.

RAM memory 82 may be used to store, copy and process the large volume of streaming video data coming into the processing device 58 from the image sensor. It can also be used as a work space to perform rapid data analytics locally on the device 10. Flash memory 84 may be used for non volatile permanent storage of important information related to the location and the operating system FIG. 14 is a top view of the antenna board. A Wifi antenna and a BTLE or bluetooth low energy antenna are shown. Both antennas operate at 2.4 GHz frequency.

The PIR sensor 72 along with a fresnel lenslet is used for motion detection, based on the principles of black body radiation. The fresnel lenslet may be flush against the front black acrylic plastic plate 204 and be color matched with the rest of the black acrylic material. In order to provide an aesthetically pleasing front face of the device 10, an exit window of dark black HDPE material in front of the fresnel lens, which is clear or whitish. The black HDPE would allow >8 um wavelengths to pass through.

Setup Procedure

In accordance with an embodiment of the invention, the device 10 may be configured or "set up" for use and transfer of information between the device 10 and a home network, as well as between the device and a user device 24, via the audio jack of a use device 24 and the device 10. Since the device 10 does not include a user interface in this example, the user interface or input of the user device, such as a keyboard or touch screen, is used to enter data. Setup in accordance with this embodiment is simple, rapid, and avoids the need for a computer in the setup process.

Figure 17A:
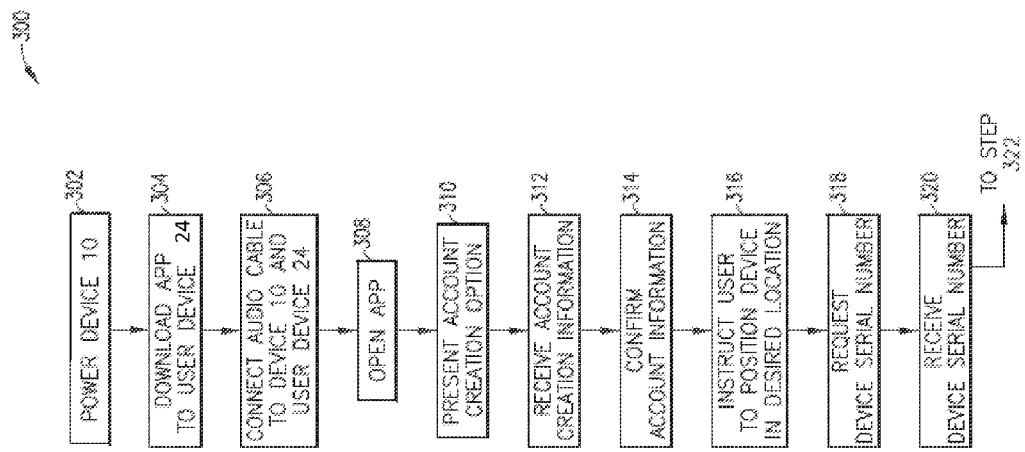
FIGS. 17A-17C show a flowchart of an example of a setup procedure, in accordance with an embodiment of the invention.
Figure 17B:
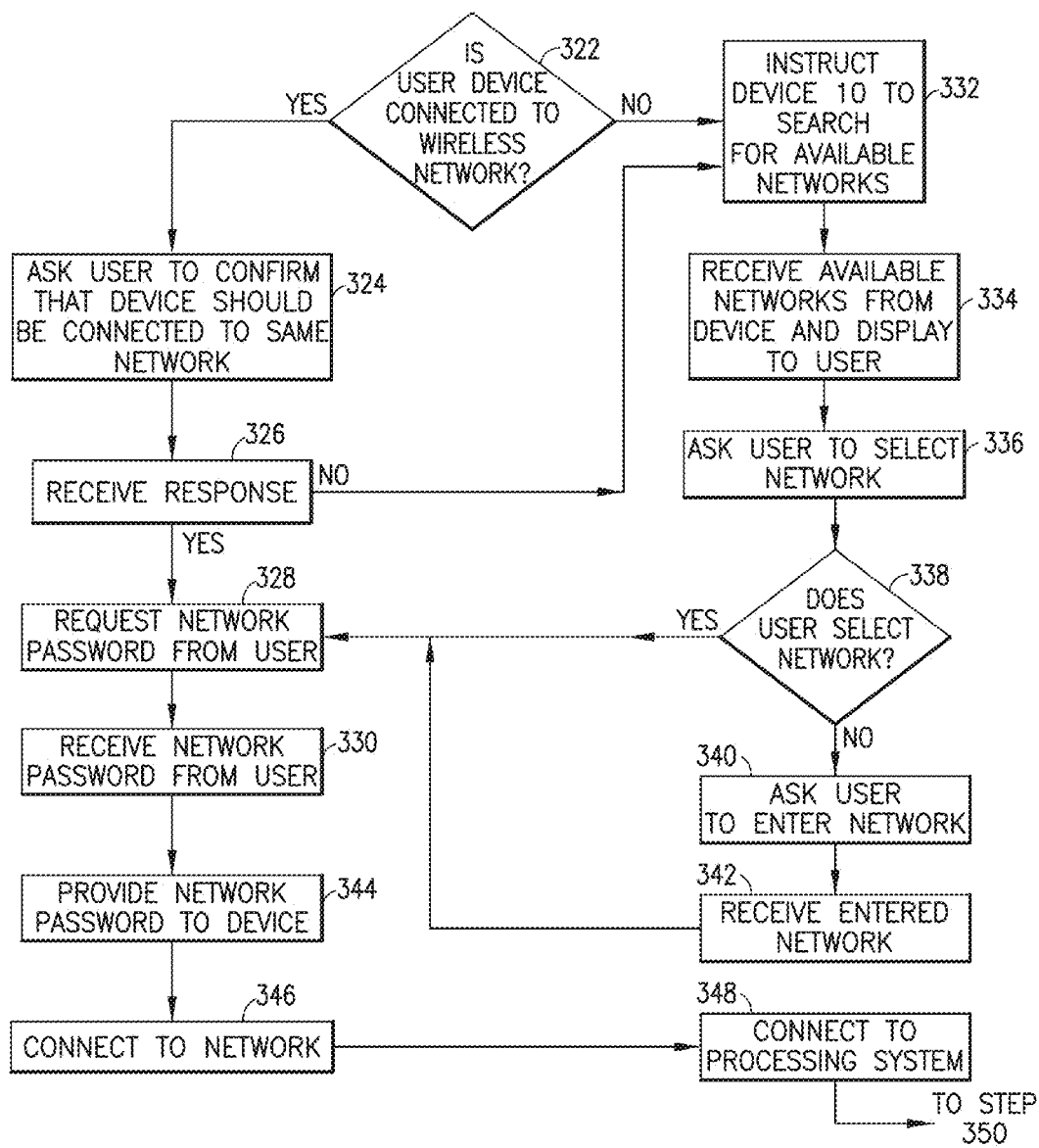
Figure 17C:
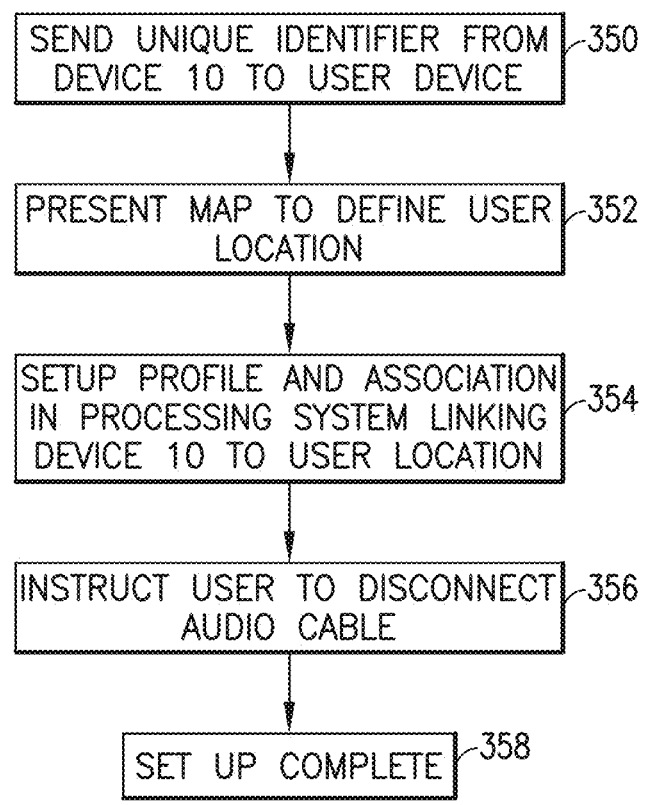

FIGS. 17A-17C show a flowchart of an example of a setup procedure 300 in accordance with an embodiment of the invention. The device 10 is plugged in or battery powered is turned on, in Step 302. The primary user 22 downloads an App to their device 24 and connects an audio cable, commonly known as 3.5 mm audio jack, to the device 10 and to the user device 24, in Steps 304 and 306. The cable is connected to the 3.5 mm audio port (stereo sound and microphone) of the user device 24, and to the 3.5 mm audio jack 96 of the device 10. The user device 10 may be a smartphone, tablet, laptop, or other computing device.

The primary user 22 can at this point set up the device either through a web interface accessed by the user device 24 or through the App downloaded to the user device 24. The remainder of the method 300 will be described with respect to an App on the user device 24. Use of a web interface is similar.

When the user opens the App, in Step 308, the App presents an option to Create an Account, in Step 310. Selection of the option causes the App to present a graphical user interface enabling the entering of a user's name, email address, password, and phone number, for example, via the input of the user device 24, such as a touchscreen or keyboard, in Step 312. Other information may be requested, as well, such as how many devices 10 are being set up and where are they located, for example. The creation of the account and the account information may be confirmed by text or email, for example, in Step 314. The user 22 may also be requested to agree to terms of service and to agree to accept push notifications, email, and/or text messages that are used to inform the primary user of events taking place in the location, as described below. The primary user 22 may be informed of events by phone, as well.

The user 24 is instructed by the App to position the device in a desired location, in Step 316. Example locations are discussed above.

The App requests the device serial number from the device 10, via the audio cable, in Step 318, and the serial number is received, in Step 320. Data is encoded as audio signals to pass from the device 10 to the user device 24, and decoded by the user device 24 via the App. The device 10 may be configured to encode and to decode the audio signal, and respond to it in order to complete the setup process, as well.

The App on the user device 24 will then determine if the user device is connected to a wireless network, in Step 322, in FIG. 17B. If Yes, the App asks the user to confirm that the device 10 should be connected to the same network, in Step 324. The response is received, in Step 326. If the user confirms, then the App instructs the device 10 to connect to the same network. The device 10 requests a password for the network, in Step 328. The user enters the password via the input device on the user device 24, such as a touch screen or keyboard. The App encodes the password into audio signals and provides the password to the device 10, via the audio cable. The App encodes the password into audio signals and provides the password to the password is received by the device 10 via the audio cable, in Step 330, and the device decodes the password. The device 10 updates the Wifi credentials, restarts the necessary systems, and connects to a processing system 14 via the network, in Step 128, in a manner known in the art. The device 10 then connects to the user device, in Step 130.

If the user is not connected to a wireless network, in Step 322, or does not confirm that the device 10 should connect to the same network, in Step 324 and 326, the App instructs the device to search for available networks, in Step 332. The device 10 informs the App of the available networks, in Step 334. The App then asks the user to select a network from the available networks, in 336. If the user selects one of the networks, in Step 338, the App requests the network password from the user, in Step 328 and the method 300 proceeds, as described above.

If the user does not select one of the networks, in Step 338, then the App requests the user to enter a desired network, in Step 340. The user enters the desired network by entering the service set identifier ("SSID") of the network, for example, via the input device. When the identification of the network is received, in Step 342, the App requests the network password from the user, in Step 328 and the method 300 proceeds, as described above.

The network password is provided to the device 10, in Step 344, via the audio cable, and the device connects to the network, in Step 346. The device 10 then connects to the processing system 14, in Step 348.

After connection of the device 10 to the network 16 and to the system 14, in Step 348, a unique identifier of the device 10 is sent by the device to the user device 24, in Step 350. This enables the user 24 to setup the device 10 as their device in the system, i.e., to be an approved and connected device from a security and administrative perspective.

A map may be presented to the user 22 via the App to identify the geographic location of the device 10, in Step 352. The App sends the User Account information established in Step 312, the serial number of the device 10, and the user's geographic location defined in Step 352, and sends it to the processing system 14, which establishes a profile and an association between the device 10 and the user's location, in Step 354.

Having set up the wireless connection and provisioning the user device 24 to know that it is working with the device 10, the user will be instructed to disconnect the audio port, and the device setup is completed, in Steps 356 and 358. If the device 10 has already been placed in a desired location, the device is ready for operation, without further installation.

A secure cryptographic key may also be issued between the device and the phone, to enable them to be paired securely. In this case, the device 10 can 'talk' to the phone itself, and know that it is the phone it paired with, by an exchange of keys.

The steps of the method 100 may be performed in a different order. Instead of asking the user 22 to confirm that the network that the user device 24 is connected to is the network the device 10 is to be connected to in Steps 316-322, the method 100 may proceed from Step 320 to Step 332, where the device 10 searches for available networks.

If a primary user 22 moves the device 10 to a new location, or changes their wireless name or password, they can update that change on the device by again connecting the user device 24 to the device 10 via the audio port 102.

Bluetooth low energy ("BTLE") communication may also be provided for information exchange, in which case the user device 24 and the device 10 will find each other before communication begins. In another set up procedure, the device 10 comprises a wireless router, allowing the user device 24 to connect to the device directly. In this example, the device 10 sends an IP address to the user device 24. The user enters their Wifi SSID and password via the App to connect to the device 10.

In other examples, Bluetooth pairing, direct USB connection, or DTMF may also be used to configure the device 10. Encoding information may also be provided into a flashing light, which is read by the user device 24.

Interaction Between the Device and a Home Network

After setup, as described above, the device 10 may be connected to the user home network, which may comprise a wireless router, Ethernet, etc., in the home, and the devices connected to it, such as desktop computers, laptop computers, mobile smart devices, etc. The device 10 may receive information and instructions from the home devices connected to the home network and from the user device 24. The device 10 may also send outbound interactions, such as information that the device 10 sends to the system 14 and to user device 24.

The device 10 communicates with the user device 24 via an App, such as the App discussed above in the set up procedure, to communicate with it the user device. Since this App may run in the 'background' or have some functionality at all times on the user device 24, it can be used for security or safety functions. For instance, when a user 22 approaches a physical location, automatic arming or disarming, based on proximity of the users of the security system 14 and the device 10 within the home may be enabled.

In this example, when the primary user 22 approaches a predetermined radius around their home 12 or other location where the device 10 is located, the user device 24 sends a signal via the App to the home network that the primary user 22 is in the area and that the device should be 'ready' for them to enter. Being 'ready' in this example means that the device 10 and the system 14 should not notify the primary user 22 immediately upon entry of the user 22 into the home 12 that someone has entered the location, despite recognition of entry by the sensors of the device 10. Instead, the device 10 and system 14 may assume that the person entering the location is likely the primary user 22 and thus it should wait another predetermined set of time, such as 45 seconds, for example, to confirm that the user is in the location through the App or wireless network and disarm itself.

Other information for the user can be sent through the App and other users can use the App. For example, if a user adds a third party as an approved user in their network, that third party can download the App to their own user device 24, and use the same proximity-based geolocation services of the device 10 to arm or disarm the user's system.

In one example, if authorized by the user, other users may be listed as primary, secondary, or tertiary users on a user's network may be able to automatically arm or disarm a device 10 without alerting the first primary user 22. A secondary user may be a family member or other person regularly in the home 12.

In one example, the information may be saved into a 'timeline' of events but the primary user 22 will not notified as if this was a security incident. Timelines are discussed further below. By including other parties in the interactions with the device 10 and the system 14, security becomes more than simply an individual within their physical network. It becomes a social construct where a large group of people are listed as 'trusted' within an environment. Such a group security, or social security construct, may improve the way people work together to protect each other. By acting together as a community, enabled through technology, the wider community becomes more secure.

Additionally, by geolocating the cell phones, other preferences in the home can be controlled. For example, the device 10 may act as a hub for other services within a home, and preferences can act differently for different people that are identified in the system. From a security and safety point of view, specific actions and notifications can be aligned with the geo-location of phones and the confirmation of the proximity of individuals within the location. An individual owner of the account can set preferences for the individuals. An action may be a specific notification—if the location of an individual's child, for instance, is activated, then the individual can receive a timeline or graph of the comings and goings of their children. In other words, specific actions based on the person.

An event is a deviation from the norm or a deviation from a predefined set of criteria in a location monitored by the device 10, for one or several of the sensors, the camera (imaging sensor 60), and/or the microphone 76. There are several methods for learning/teaching the system to know what is normal or ordinary in a home or other such location in which the device 10 is situated, and what is not normal or out of the ordinary or a deviation, in accordance with embodiments of the invention.

Preset Parameters

The system 14 may define certain parameters or criteria concerning what is normal and what constitutes an event or incident. For example, the system 14 may define that a temperature above a certain threshold should cause a notification. The parameters may be based on the geographic location of the device 10 and the home 12. For example, temperature parameter and/or humidity criteria in a geographic location having high average temperatures and/or humidity may be higher than the temperature and/or humidity criteria for geographic locations with lower average temperatures and/or humidity. The temperature parameter may also be change seasonally, based on the current date. Air quality parameters levels may be similarly defined by the system 14. The parameters set by the system 14 may include a combination of sensor data. For example, a notification may be sent only when both the temperature and humidity and/or air quality are above predetermined levels. Criteria and parameters may be stored by the system 14 in the database 20, for example. Criteria and parameters to be applied by the device 10, if any, may be downloaded by the system 14 to the device through the network 16, for storage in the RAM 82 and/or the flash memory 84 or other such memory, for example.

User Parameters

The primary user 22 may set certain parameters and criteria for what is considered to be an event and when notifications should be sent. The parameters set by the user 22 can apply to one or multiple sensors, as discussed above. The parameters and criteria may also include a combination of sensor data and circumstances. For example, a primary user 22 can specify that they only want to be informed of an event if no one is home and if there is noise above a certain decibel. Or, a primary user 22 can specify that any time a specific person comes into their home 12 the primary user 22 wants to be notified or wants another person to be notified. In another example, a primary user 22 may determine that any time a certain person or user is inside a home and the temperature goes above or below a certain value, the primary user is to be notified. These are merely examples of parameters and criteria that a user can set. User parameters may be set during the on-boarding process and/or after on-boarding, where questions are posed to the primary user 22 to establish the user defined parameters and criteria, as discussed further below.

Learning Via User Habits, Behavior, and Feedback

In addition to user parameters and preset parameters, the device 10 and/or the system 14 is configured to learn from a user's behavior and the activities in a user's home 12, to further define what is normal activity in the home. The processing device 18 in the system 14 and/or the processing device 58 in the device 10 may be configured to learn by software stored on respective storage devices, such as the database 20 and the RAM 82 or the flash storage 84, or other appropriate memory or storage devices.

The learning process may begin with basic patterns within a home, such as the comings and goings of people within a home based on the day of the week and time of the day. Most people have somewhat standard behavior which can be understood by the device 10 and/or system 14. For example, the system 14 may know how many people are in the house 12 and who they are based on user input or by sensing body mass and activity by the one or more sensors on one or more devices 10 in the home, and/or by geo-location data. Individual patterns of those people, such as when they come and go from the location on each day of the week. If over 2-4 weeks a respective person has acted regularly over a time period, a pattern may be established for that person. If the primary user is notified of the person's activities in accordance with the pattern multiple times and the primary user clears the event, such as the person entering the home 12 at a particular time, the next time the person enters the home in accordance with the pattern, the primary user will not be notified of the event. The event may be stored for future reference, such as in a timeline that can be provided to the primary user 22 upon request, if desired.

Patterns may be discerned for environmental characteristics of the home or other location based on sensor data, as well. For example, patterns related to temperature, humidity, and/or air quality may be discerned by comparing the data from the temperature, humidity, and/or air quality sensors over a period of time.

The system 14 may use data from the image sensor 60, which may be in the form of video, for example, along with audio input from the microphone 76, and/or temperature and humidity inputs from the temperature/humidity sensor 90/88, for example, to learn about the activities of a user in a given location, and the level of activity in the location. This enables the system 14 to determine a normal level of activity in a given location, such as in a given room in the home 12. If high activity is normal at particular times of a weekday or a day of the weekend, for example, and the system 14 determines that there is very little activity at one of these times, it may be because the user went on vacation, for example, or it may be that there is a potential problem. The system 14 identifies the deviation from the norm and notifies the primary user 22. The user 22 can approximately then respond to the notification.

Additionally, if one device 10 within a location detects a pattern, the pattern can be set for all the devices in the location. One device 10 can also break a pattern by another device. For instance, one device 10 does not detect movement and therefore thinks that no one is in the home 12 during a certain time of day, and another device 10 within the home detects movement, that input is calculated in a per-location basis and the pattern of the first device is trumped by the input from the second device. The system 14 accumulates information from multiple devices 10 to determine current activity and patterns of behavior, in a location.

The identity of persons within a location may be determined by the system 14 based on patterns learned about respective persons. Those patterns include general size and weight of the user, as determined by data received from the imaging sensor 60 and PR sensor 72, for example, the level of heat generated by the person, as determined by the PR sensor, for example, the voice of a person, as detected by the microphone 76, the facial or other pattern recognition of the user based on data collected by the imaging sensor, activity patterns of the user based on learned patters, or other person specific data determined via the various sensors within the device 10. Person recognition is important in order to determine the activity and patterns of individual members of the location, to know who is home to determine if there are individual-specific responses to incidents.

The presence of pets in a location based on video data collected by the image sensor 60 and infrared heat showing the approximate size and shape of an animal detected by the PR sensor 72, as well as sensitizing and de-sensitizing certain video pixels, such as by highlighting a portion of the video which is less sensitive to pets and movement, should there be an area where a pet constantly passes. Questions presented to the user during on-boarding may be used in conjunction with the sensor data to recognize pets. It is noted that pets are a common source of false alarms in home security systems. By learning to recognize the presence of pets, false alarms may be reduced.

One of the ways the system 14 and the device 10 enables learning is by giving status scores a home 12 or portions of the home activity. For instance, if a user's home 12, or a particular room in the home, is typically very loud and very active at certain times of particular days, based on noise detected by the microphone 76, motion found in the video recorded by the image sensor 60, and/or temperature/humidity fluctuations detected by the T/H 99/88, for example, the home 12 or room in the home may be assigned an activity score of 10/10 for those times of those days. Activity scores may be stored in the database 20 in the system 14, in association with the time period of the particular days that the score is applicable, the room the score is applicable to, and identifying information about the user and/or the user's home, for example. In one example, if a current activity score drops more than 20% below the expected score in a time period, the primary user 22 may be alerted. Other percentage deviations or ranges may be used instead.

In another example, a home 12 including an elderly user who lives alone may have a low activity score of 2, for example. If the activity score in the elderly person's home 12 suddenly rises to 5, that also may be indicative of a potential problem, such as a home intrusion, or the rise in the activity score may be caused a visit by grandchildren, for example. By notifying the elderly user and/or the person's backup contacts of the noted change in activity, the user or backup contacts may inform the system that there is or is not a problem in the home.

Other characteristics of a location may be assigned scores based on other sensor data, such as scores for temperature, humidity, and/or air quality, for example. By scoring both the sensors themselves and the sensors working together, the system 14 can provide a clearer and complete picture of what is normal or not normal in a home 12 or other location, and respond accordingly.

The device 10 and/or the system 14 enable learning by recalibrating how sensor data is processed. For example, the device 10 and/or the system 14 may enable learning by adapting how the processing device 58 and/or the processing device 18 processes data about a location based on one or more pieces of data about the location that are collected by one or more sensors coupled to the processing device, for example.

On-Boarding Process

Embodiments of the invention include a learning-based on-boarding process. In one embodiment of the invention, during the initial stages of ownership of the product such as the first two weeks, for example, there is a rapid learning period, which includes periodic questions to determine information on the home 12 or other environment where the device 10 is located, such as:

What is your address?
How many people live in your house?
How many are adults?
How many are children?
Do you have pets?
If you have pets, how many and what are the types?
What time do you usually leave for work?
What time do you usually come home from work?
Do you have any predetermined days when you arrive home later than or earlier than usual (such as a regularly scheduled meeting or exercise)?
What time do your children leave for school?
What time do your children usually return home from school?
Do your children have regular activities that make them arrive home later than usual?
Do you have regular visitors on any days of the week, such as a housekeeper, dog walker, etc.?
What time is your mail delivered?
What time is your newspaper delivered?
Do you use air conditioning? If Yes, is it on a schedule? If so what is the schedule?
Is your thermostat on a schedule? If so, what is it?
Who will be your back up contacts?

The questions above are merely examples and are not necessarily in the format that would be presented to a user 22. These questions express the subject matter of possible questions and information that may be desirable to collect. The questions may be presented as multiple choice questions and/or as fill in the blank questions, with dropdown menus and/or windows addressing user input words, names, times, etc.

It is not necessary for the user 22 to answer all of the questions, but the more questions answered, the faster the system 14 will learn the normal activities in the home 12 or portion of the home or other environment, at different times of the day and days of the week. The answers to those questions will inform the learning software and the learning software. For example, since the system 10 now knows that if the user has pets, it is necessary to differentiate between the movement of the pet and the user and other household members.

Periodic questions to confirm what is learned about the environment may also be presented to the primary user 22. For example, the system 14 can deduce a pattern as user patterns of coming and going then it can ask the user to confirm that that pattern of activity or learning is accurate. In particular, if the device 10 sees over a period of days or weeks that a certain activity, such as people waking up, adults leaving and returning from work, children leaving and returning from school, deliveries, such as newspaper, laundry, and/or mail deliveries, etc., happening at a certain time times that have not been addressed by a response of the user to on-boarding questions, then the system 14 can ask the user to confirm that that pattern of activity or learning is accurate. The learning may involve a combination of observed behavior and previously answered questions by the user. Other patterns may relate to temperature, humidity, and/or air quality changes over the course of the day, for example.

Score and Rewards-Based Incentives Learning

Providing a 'completeness score' on how much the device has learned, and how much is left to truly understand the behavior of the individual, may encourage primary user 22 to answer more questions for example. If over a series of weeks the device 10 has observed the primary user's behavior, and has had a number of questions answered by the user, then the system 14 can inform the user 24 how close it is to knowing their environment by giving the user a completeness score, such as that learning is 80% complete, for example. The system 14 may always be learning, and can learn new patterns so the completeness score can continue to evolve. The score can be given as a percent or in another form, including natural language.

Percentage of completeness or other such score may also be awarded for the various tasks the user has to perform as a part of the on-boarding process learning process, such as answering the questions presented, as well as other activities, such as adding their friends and family as backup contacts 26, confirming the identity of the local police 28, fire department 32, and ambulance service 34, for example.

Rewards may be based on the completeness of the profile. For example, providing extra storage in the database 20 in return for completeness of the on-boarding process. Such additional storage may be used to store video clips that a user is interested in, for example.

Data Activity Score

As the device 10 gathers data through its sensors, that data may also be given a sensor activity score. The score is based, at least in part, on a particular point of data from one sensor or a data set from multiple sensors, and what is learned about the location. After learning the patterns of room or home, for example, throughout a day and week, such as the frequency of movement or average temperature, the device is able to determine a baseline of activity or events that are deemed normal in a particular location and during particular times of a day. When new data is acquired by the device's sensors, that data's issue activity score is determined against the baseline of what the device has learned to be normal at that time of the day and day of the week in order to identify potential threats. The data is compared to the pattern or patterns by the system 14 and/or the device 10 and the degree deviation from the normal pattern may be determined, for example. The deviation may be expressed by a percentage deviation, for example. The degree of deviation may also be applied to a scale of 1-10 or 1-100. A higher percent deviation or issue activity score reflects a stronger deviation from the homes normal baseline. Sensor activity scores may also be indicative of the comfort of the physical environment of a home is, when certain sensors such as temperature deviate from the baseline pattern or a threshold set by the primary user 22, for example. The user may be informed of the deviation in terms of the degree of deviation as a percentage or score, for example.

During operation, the device 10 may continuously collect data from all the sensors while on or during other time periods. Sensor data may also be periodically collected and stored, at regular or non-regular time interval. Some or all of the collected data may be analyzed by the processing device 58 on the device 10, and/or sent to the system 14 via the network 12 for analysis or further analysis. Collected and stored data may be sent to the system 14 for analysis continuously or periodically in regular or non-regular time intervals as well. The data or data files may be sent by the device 10 to the system 14 with metadata including an identification of the device it is coming from, along an encrypted channel such as a secure socket layer (SSL) connection. The collected data may be sent in multiple respective data streams or in other formats, for example.

Figure 18:
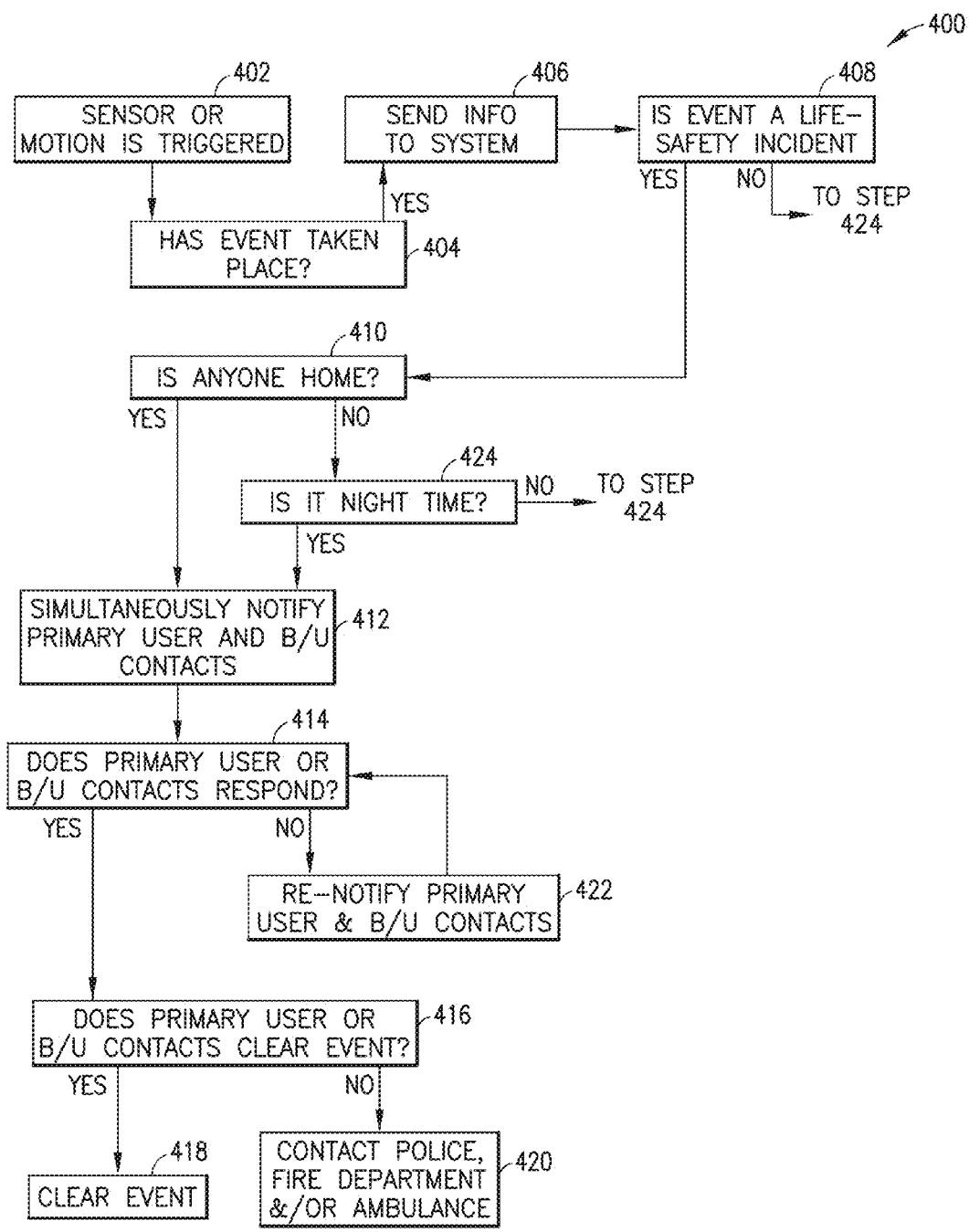
FIGS. 18 and 19 show a flowchart of an example of a method of the operation of the device and the system in response to an event detected by the device.
Figure 19:
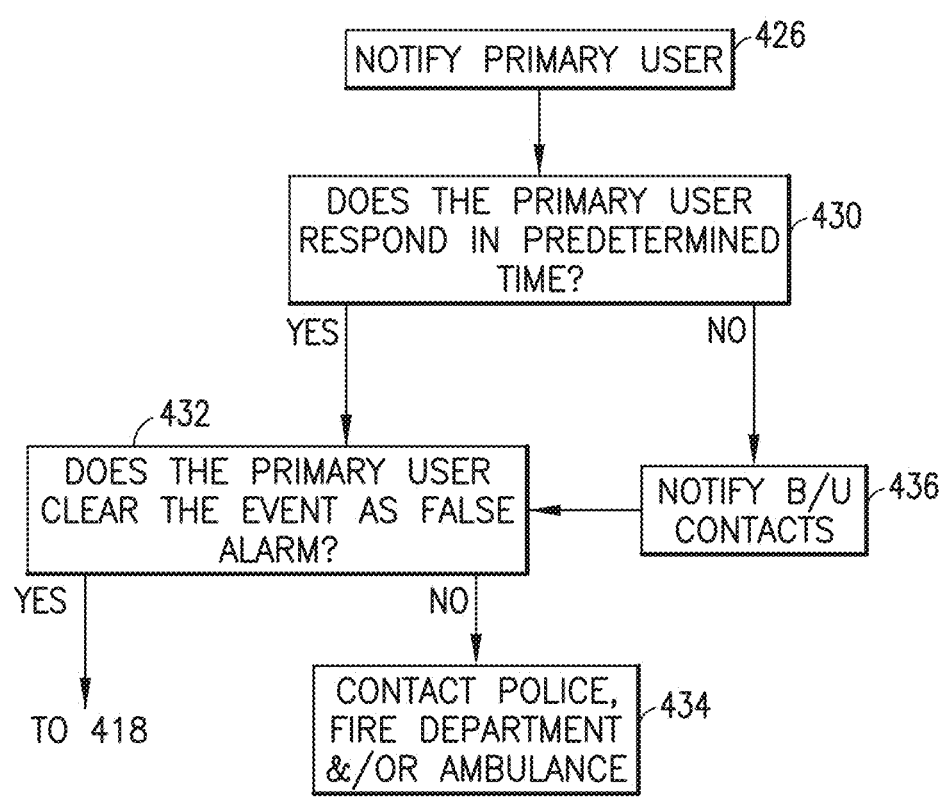

FIGS. 18 and 19 show an example of a method 400 of the operation of the device 10 and the system 14 in response to an event detected by the device 10. One or more sensors are triggered and/or motion is detected, in Step 402. In this example, the device 10 determines whether the detected data is to be defined as an "Event" that needs to be further analyzed, in Step 404 based on whether the detected data meets criteria, such as exceeds a threshold, or is a deviation from a pattern, for example. If not, in this example, no further action is taken. If Yes, the device 10 sends the detected data and other information related to the event to the system 14 via the network 16, in Step 406, for further analysis. The data sent by the device 10 includes the data from the sensor or sensors triggering the event, and data from other sensors, which may assist the system 14 in the interpretation of the data from the sensor triggering the event. For example, if the temperature sensor 90 is triggered, a video clip may be sent to be the system 14, as well. Identification information related to the device 10, the user 22, the home 12, the location of the device in the home, etc., may also be sent.

In this example, the system 14 determines whether the event is a life or safety incident based on the received data, in Step 408. A life or safety event may be detection of a high temperature by the temperature sensor 90, very poor air quality as sensed by the air quality sensor 94, excessive and sudden noise, as measured by the microphone 76, etc. The detected characteristic may be compared to thresholds or other such criteria to determine whether the detected characteristic qualifies as life threatening, for example. The event may be based on a combination of sensor measurements, as well.

If the event is a life-safety event, it is then determined if anyone is home, in Step 410. The system 14 may know whether anyone is home based on data previously received from the image sensor 60, the PIR sensor 72, the microphone 76, and geo-location of user devices 24, for example.

If Yes, then the system 14 treats the event as an emergency and simultaneously contacts the primary user 22 and backup contacts 26 in Step 412, via email, text, and by phone, for example. Primary users 22 may determine how they are to be contacted. Different backup contacts may be contacted depending on the type of the event.

It is determined whether the primary user 22 or backup contact 26 responds within a predetermined period of time, in Step 414. The predetermined time may be one (1) minute, for example. If Yes, it is determined whether one of the contacted parties clears the event as a false alarm, in Step 416. If Yes, the method ends in Step 418 with the event being cleared.

If the event is not cleared in Step 416, then the system 14 will take further action, in Step 218, such as to call the police 28, fire department 30 and/or ambulance service 32, police and/or fire department depending on the event. The system 14 may cause the device 10 to activate the siren 86, as well.

If the primary user 24 or backup contacts 26 do not respond, in Step 414, then they are re-notified, in Step 422 and the method returns to Step 414. If the primary user 24 or the backup contacts 26 do not respond in Step 414 after re-notification, the system 14 may proceed directly to Step 420 to call the police, fire department, or ambulance.

If no one is home, in Step 410, but it is determined that it is nighttime, in Step 424. The system may still treat the event as an emergency and proceed to Step 412.

If the system 14 determines that the event is not a life threatening event, in Step 408 or that is not nighttime, in Step 424, the primary user is notified in Step 428. If the primary user 22 responds within a predetermined period of time, such as one (1) minute, for example, in Step 430, it is determined whether the primary user cleared the event as a false alarm, in Step 432. If Yes, the alert is cleared, in Step 418, as discussed above.

If the primary user 22 does not clear the event as a false alarm, in Step 432, the method goes to Step 434 to contact the police, etc., which is also discussed above.

If the primary user 22 does not respond in the predetermined period of time, then the backup contacts 26 are notified, in Step 434. It is then determined whether the backup contacts clear the event as a false alarm, in Step 432. If Yes, the event is cleared, in Step 418. If No, the system contacts the police, fire department, and/or ambulance service in Step 434.

Figure 20A:
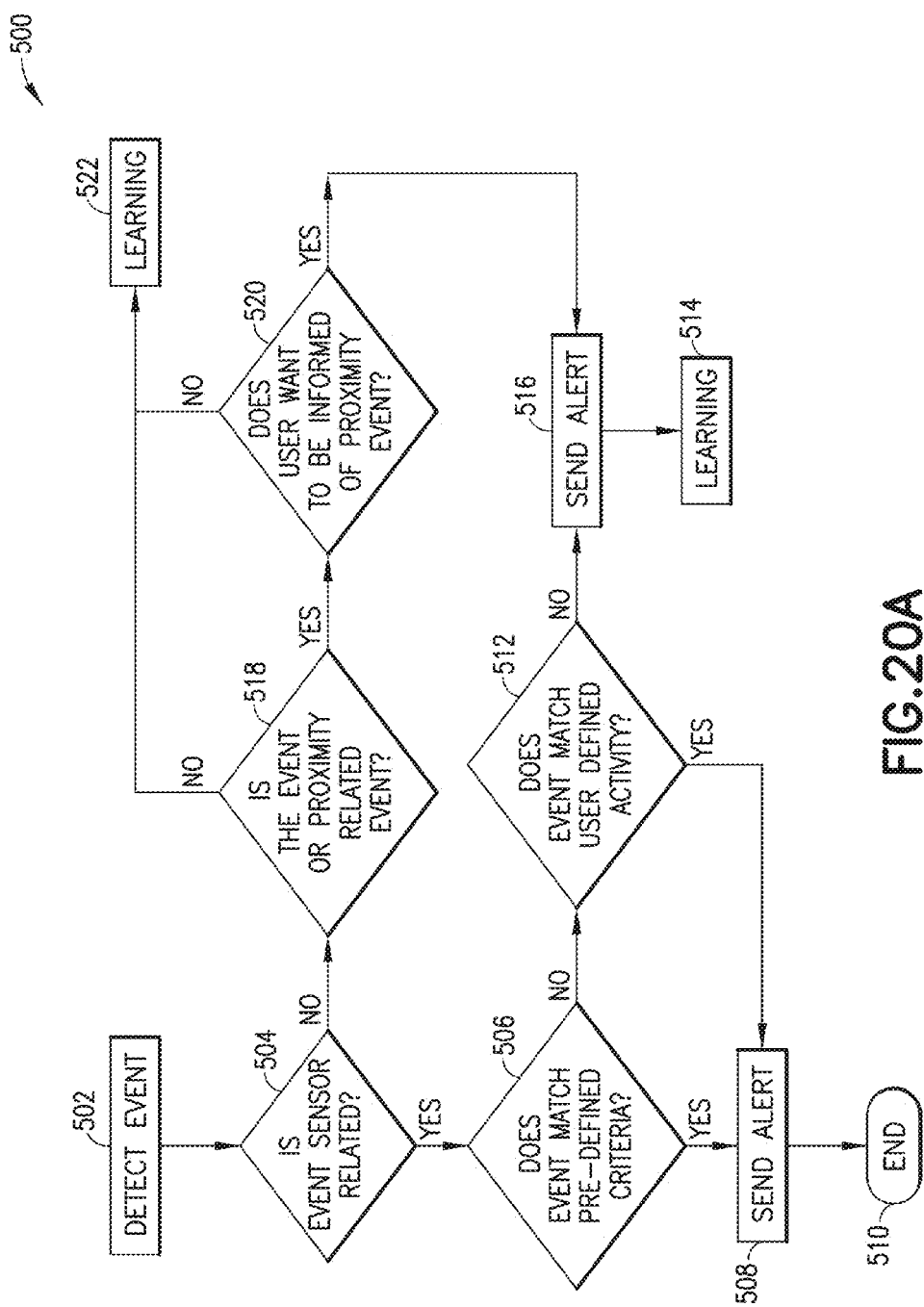
FIG. 20A is another flowchart of an example of a method of operation of the device and/or system when an event is detected, in accordance with an embodiment of the invention.

Steps 426-436 show an example of how the system 14 can escalate notifications from the primary user 22, to the backup contacts, 26, to the police, etc. The escalation procedure may be determined by the system 14 and/or by user preferences. A primary user 22 may set the time period before a backup contact is alerted after the primary user 22 has failed to respond and resolve a notification, for example. Other escalation policies that can be set by the primary user include: the types of alerts that are escalated (i.e. only alerts from certain sensors are sent to a backup to resolve); the time between escalation as between backup contacts 26 if not all backup contacts were initially contacted; if neither a primary user of backup contact has resolved an event automatically sound the siren; if no one responds alert the authorities (via call center backup for users who opt in to the service plan);

FIG. 20A is another example of a method of operation 500 of the device 10 and/or system 14 when an event is detected in accordance with an embodiment of the invention. In this example, the device 10 performs all the steps of the method 500 except for the learning steps, which are performed by the system 14.

An event is detected, in Step 502. It is determined whether the event is a sensor related event, such as an event detected by the temperature/humidity and/or air quality sensors, in Step 504. If Yes, the device 10 determines whether the event matches pre-determined criteria for sending an alert, in Step 506. As, discussed above, the pre-determined criteria are system defined criteria, such as thresholds. If Yes, then the device 10 sends an alert to the user 22 in Step 508 and the method ends in Step 510.

If the device 10 determines that the event does not match pre-defined criteria in Step 506, the device determines whether the event matches user defined criteria, in Step 512. As discussed above, user defined criteria are criteria set by the primary user 22. In other words, the primary user 22 informs the device 10 and/or the system 14 that a notification should be sent when particular criteria are met. The user defined criteria may be defined by the primary user 22 through the questions asked by the system 14 and answered by the user during set up and during operation, as discussed above. If the device 14 determines that the event meets user defined activity, in Step 512, an alert is sent to the primary user 22, in Step 508. Escalation may be followed if the primary user 22 does not respond in a predetermined period of time, as shown in FIG. 19, for example and discussed above.

If the device 10 determines that the event does not relate to user defined criteria, an alert is sent in Step 416 and the event is submitted for learning to the system 14, in Step 518.

If the event is not determined to be sensor related by the device 10, in Step 504, then the device 10 determines whether the event is proximity related, such as a person entering the home 12, in Step 516. If Yes, the device 10 determines whether the user wants to be informed of a proximity event, in Step 520. If Yes, an alert is sent by the device, in Step 420, and the event is submitted to the system 14 for learning, in Step 418. If No, then an alert is not sent and the event is submitted to the system 14 for learning, in Step 422.

If the event is not related to a sensor event, a proximity event, or predefined criteria, then the system can also learn from the event. The event may relate to data collected by the camera/imaging sensor 60, and/or microphone 76, such as sudden or unaccounted for motion or noise, etc. The event may be presented to the primary user 24 and the user can input information clearing the event or defining the event. In this way, the system 14 learns which events the primary user wants to be informed of, and which events the user does not want to be informed of.

For example, the video may show a small mass moving close to the floor. When presented to the primary user, the user may identify this mass a pet. After the user identifies a small mass moving close to the floor as a pet two or three times, the system 14 learns not to send an alert the next time a similar moving mass is identified.

In another example, a person of a particular size and shape may enter the house between 9-10 AM on a Monday. An alert is sent to the user, who clears the alert. The same event takes place on the next two Mondays, which are also cleared by the user. The system 14 can then ask the primary user 22 whether it is necessary to send alerts the next time the same person of the same size and shape enters the house on a Monday between 9-10 AM.

In another example, noise of a common low frequency may be detected for 7 or more days in a row. The system 14 can learn that this is a normal level and only send alerts if the noise level suddenly spikes above this usual level, even if the spike does not exceed a preset threshold previously set by the system 14, for example.

In another example, the system 14 may detect a loud noise at the same time every day, for 7 days. Each day the primary user 22 clears the noise event. The next day the system 14 detects the same sound at the same time, and does not send an alert to the user.

While the device 10 performs all the steps of the method 400 in the description above, the device 10 and the system 14 may both perform steps of the method. For example, the device 10 may perform all the steps except for the learning steps 414 and 422, which are performed by the system 14. In another example, the system 14 is configured to send the alerts in Steps 408 and 416. In another example, the device 10 detects an event and provides the information related to the event to the system 14, which performs the remainder of the steps of the method 400. In another example, the device 10 provides all data collected from all the sensors to the system 14, which determines whether an event has taken place, and performs all the other steps of the method 400.

While referring to the device 10 and the system 14, it is understood that actions taken by the device 10 are performed by the processing device 58 in this example, under the control of software, such as an Application stored in memory, while actions by the systems 14 are performed by the processing device 16, under the control of suitable software stored in memory. As noted above, the system 14 may be a discrete entity or a cloud based processing system.

Figure 20B:
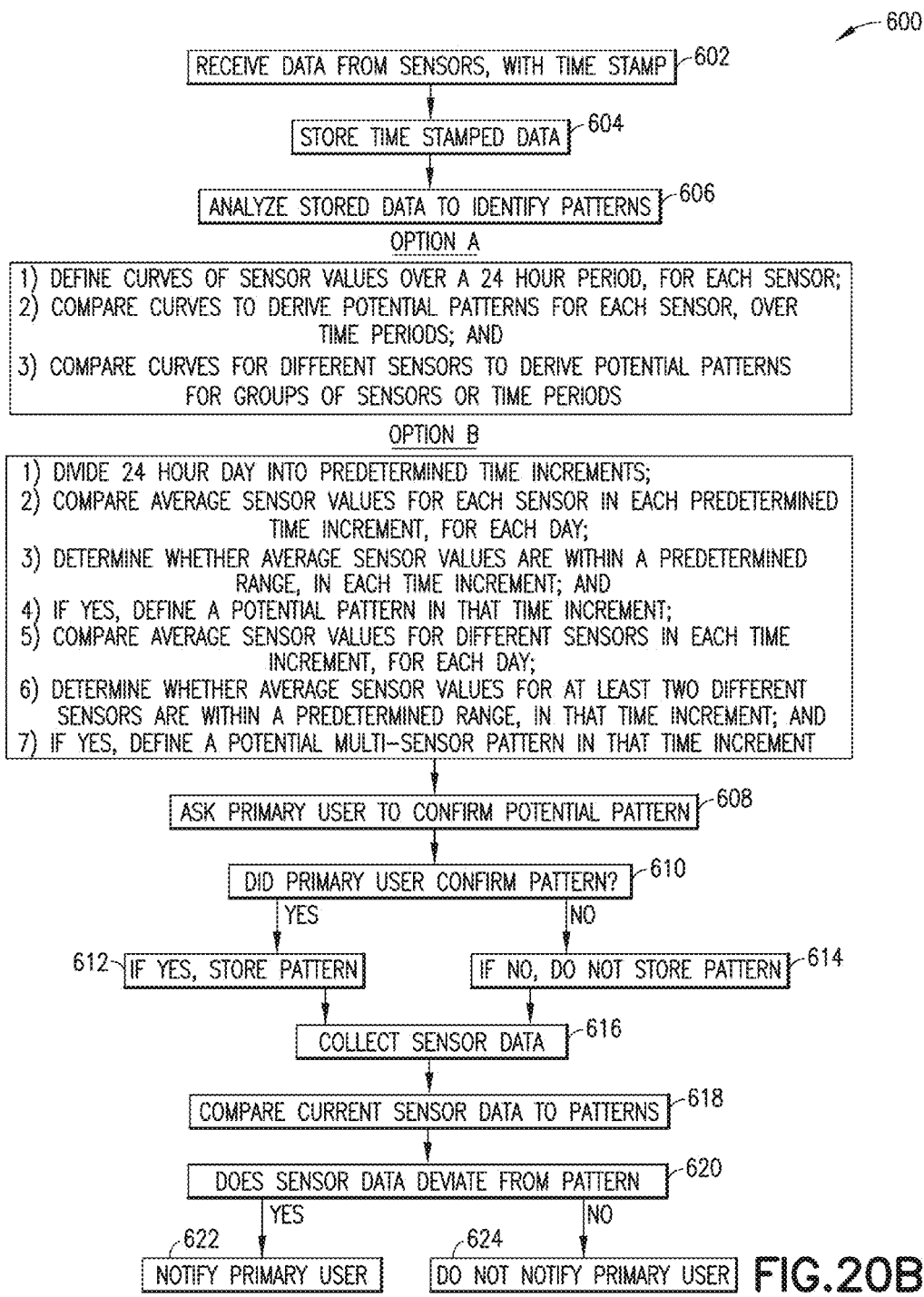
FIG. 20B is another example of a learning procedure, in accordance with an embodiment of the invention, in accordance with an embodiment of the invention.

FIG. 20B is another example of a learning procedure 600, in accordance with an embodiment of the invention. Data is received from the sensors in the device 10, in Step 602. The data includes a time stamp stating the time and date of the data, as well as identifying information, such as the device detecting the data and the location of the device in the user's home, for example.

The time stamped data is stored, in Step 504, and analyzed in Step 506 to identify potential patterns. Patterns may be identified by methods known in the art.

Two examples are described in the flowchart 600. The first Option A comprises:

1) Defining Curves of Sensor Values over a 24 hour period, for each Sensor;

2) Comparing Curves to Derive Potential Patterns for each Sensor, over Time Periods; and 3) Comparing Curves for different Sensors to Derive Potential Patterns for Groups of Sensors or Time Periods The second Option B comprises:

1) Dividing 24 hour day into Predetermined Time Increments, such as 15 minute increments;

2) Comparing Average Sensor Values for each Sensor in each Predetermined Time Increment, for each day;

3) Determining whether Average Sensor Values are within a Predetermined Range, in each Time Increment; and 4) If Yes, defining a Potential Pattern in that Time Increment;

5) Compare Averaging Sensor Values for different Sensors in each Time Increment, for each day;

6) Determining Whether Average Sensor Values for at least two different Sensors are within a Predetermined Range, in that Time Increment; and 7) If Yes, Defining a Potential Multi-Sensor Pattern in that Time Increment.

After a pattern is identified, in Step 606, the primary user is asked to confirm the potential pattern, in Step 508. If the pattern is confirmed by the user, it is stored, in Step 612. If it is not confirmed, it is not stored.

Current sensor data is compared to stored patterns, in Step 620. If the current sensor data deviates from the pattern by a predetermined amount, the user is informed, in Step 622. If the sensor data does not deviate from the patter by the predetermined amount, the user is not informed, in Step 624.

The user's response to being informed of a deviation may also be used in the learning algorithm for additional learning, as discussed above. For example, if a primary user 22 is notified of a particular deviation several times and each time the user clears the notification, the system 14 can ask the user whether the user wants to be informed of such notifications. If the user's response if No, then notifications will not be sent for the same deviation again.

Video Processing

During monitoring of a location by the image sensor 60 of the device 10, there may be long periods of time when the images do not change because nothing is happening in the environment at the location. For example, no one may be home, no one may be in or passing through the room being monitored, or the people in the room may not be moving for at least part of the time they are in the room, such as if a person is sleeping or watching television, for example. In accordance with embodiments of the invention, video recorded by the image sensor 60 is analyzed by the processing device 58 of the device 10 and/or by the processing device 18 of the system 14. In accordance with one embodiment of the invention, video is initially analyzed by the processing device 58 of the device 10 and when interesting video frames are identified, they are sent to the system 14 via the network 12 for further analysis by processing device 18 of the system 14.

Figure 21:
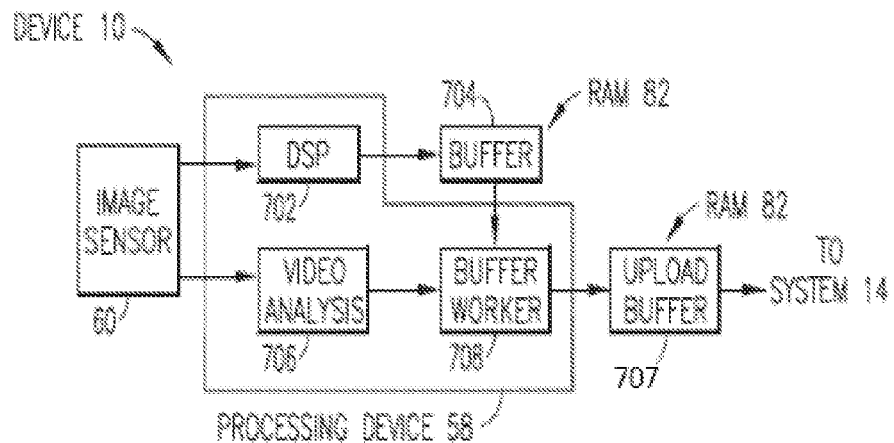
FIG. 21 is a schematic diagram of an example of components of the device involved in video processing, in accordance with an embodiment of the invention.
Figure 22:
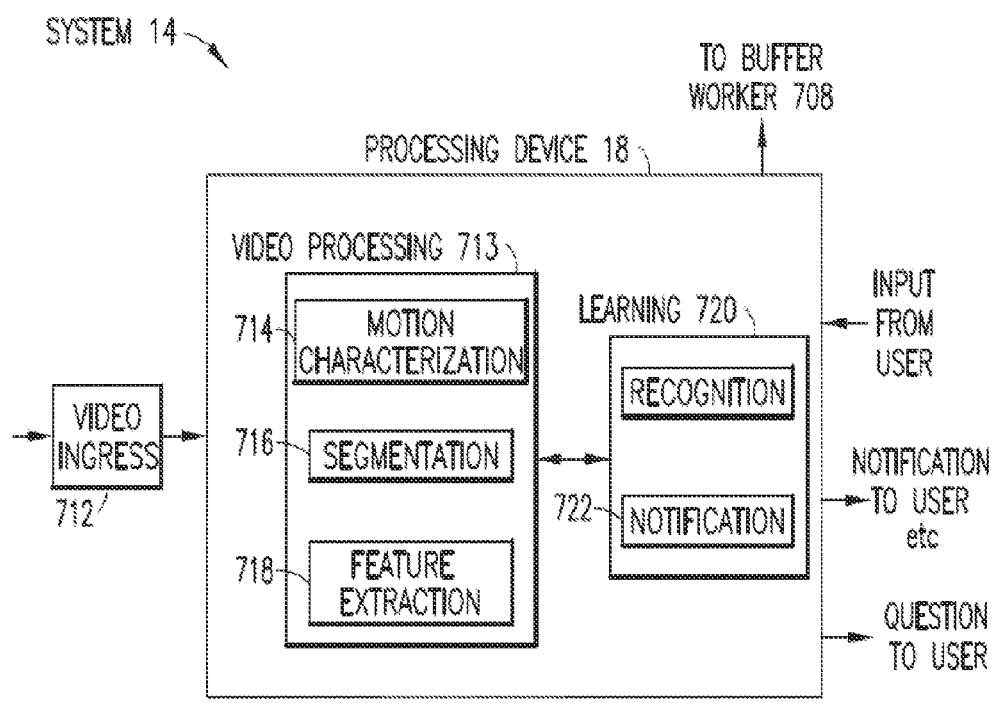
FIG. 22 is a schematic diagram of an example of the components of the system involved in video processing, in accordance with the embodiment of the invention.

FIG. 21 is a schematic diagram of an example of components of the device 10 involved in video processing, in this embodiment. FIG. 22 is a schematic diagram of an example of the components of the system 14 involved in video processing. Data collected by the image sensor 68 is provided to the processing device 58 in two identical streams. A digital signal processor 702 of the processing device 58, or a separate digital signal processor, compresses the video in one of the streams, and stores the compressed stream in a storage buffer 704. The storage buffer may be in RAM 82 or other such memory, for example. MPEG-4 video compression may be used, for example.

The second stream, which is not compressed, is provided by the image sensor 60 to the video analysis module 706 of the processing device 58. The video analysis module 706 is a software module that determines whether there is change worthy of further processing by the system 14, such as movement in the frames of the video.

The video analysis module 706 may quantify the amount of change in the video and compute an "interestingness" score, which may be a weighted function including available bandwidth between the device and system 14. The weighted function may be updated based on information/instructions from the system 14. The interestingness score may be provided to the buffer worker module 708. The buffer worker module 708 is a software module that determines which compressed frames are to be sent to the upload buffer for upload to the system 14 for further analysis.

If the interestingness score for a chunk of video is greater than a threshold, for example, the buffer worker module moves the video from the buffer storage 704 to an upload buffer 707, for upload of the corresponding chunk of compressed video to the system 14 via the network 12. The video chunk may be uploaded to the system 14 by Wifi or Ethernet, for example. If the score is less than the threshold, nothing is done. When the buffer worker 708 notices that the buffer storage 704 is near capacity, it deletes videos based having the least interesting score, the oldest video, or other basis, to maximize information stored in the buffer.

Video chunks uploaded to the system 14 are received by a video ingress module 712 in FIG. 22, via the network 12. The video ingress module 712 provides the video chunks to a video processing module 713 of the processing device 18 for video processing. Processing may include motion characterization 714, such as "entering", "leaving" "crossing" "getting up", segmentation 716, and feature extraction 718. It is noted the processing may be performed by a discrete entity or a cloud based system.

Segmentation 716 defines the moving object with respect to the non-moving background, over a number of frames. In feature extraction 718, particular features are extracted from the segmented volumes that may facilitate recognition of the moving object. In addition features are extracted from the non-moving parts of the background for characterization.

The output of the video processing module 713 is provided to a learning module 720, which performs recognition to identify the moving objects. A notification module 722 then determines whether the primary user 22 or another party, such as backup contacts 26, need to be notified of the identified moving object. If so, the notification module 722 sends the notification to the primary user 22 or other such party, via the network 12 in the manners specified by the primary user 22 and the backup contacts 26. If not, then a notification is not sent.

The learning module 720 may also provide feedback to the buffer worker 708 in the device 10 via the network 12, to adjust the threshold of the interestingness score or to mask parts of the image to remove them from the computation of the interestingness scores, such as a constantly changing television screen or a ceiling fan. While moving, a TV or fan is typically not of interest and can be considered part of the background. If not enough data is being provided to successfully identify moving objects, for example, the threshold may be lowered so that more video data is provided to the system 14 for further analysis. This may become apparent if the system 14 needs to keep asking the user to identify the same person, for example. If the system 14 determines that too much data is being provided for efficient, timely analysis, or it is determined that moving objects can be consistently and successfully identified with less data, the threshold may be raised.

During the onboarding phase or when a moving object in a section of video cannot be identified, the learning module 720 may send the video or an image to the primary user 22 with a request to identify whether an object in the video is a person, a child, or a pet. If a person or child, the system 14 may also request an identification of the person or child. The primary user 22 may also be asked whether the user wants to be informed of the presence/movement of that person, child or pet. Based on the feedback from the primary user 22, the system 14 learns the identities of people living in or visiting a home or other location. The system 14 also learns when the primary user does not want to be notified of detected movement and when the user does want to be notified of detected movement.

Returning to the operations performed on the device 10, the video analysis module 706 may determine whether the received video indicates movement by comparing a current frame or portion of a frame to a prior frame or portion of a frame, for example. In one example, a grid may be superimposed on an image. For each point in the grid, an 8×8 or other size pixel patch is defined and compared to the same size pixel patch around the same point in the prior or following frame. Differences from frame to frame may indicate movement of one or more objects within the frame. Motion vectors may be generated from frame to frame. If there is no movement, the motion vectors in a patch equals zero (0) and the prior patch with a non-zero motion vector is carried over for comparison with a subsequent patch, as in MPEG-4 video compression.

In another example, feature detection and recognition techniques, such as those used in computer vision, are used by the video analysis module 706. Instead of a grid, in this example, areas of high contrast are identified in a frame, to identify salient image areas. The most salient image areas may be identified in each frame. The salient image areas are compared from frame to frame to detect movement. Frames showing movement are given a higher interestingness score by the module 706.

The threshold compared to the interestingness score by the buffer worker may be set in the device and/or provided by the system 14 via the network 12. The threshold may be changed by the system 14, as discussed above.

Returning to the system 14, during recognition, a motion analysis module in this example determines "where" the motion is taking place in a frame and an object analysis module determines "what" is moving. Moving "blobs" may be identified moving across frames, and motion signatures of moving blobs may be determined by defining a moving vector over multiple frames, such as 150 frames, for example. Clustering may be performed of all sets of vectors to group similar motions together. These clusters may form the basis of a dictionary of "motion signatures" against which future motions may be compared.

Motion signatures in the dictionary may also be compared to signatures developed during the learning process and named by user input or comparison against all motions recognized in all devices. Motion signatures for pets will be different than that of children and adults. Entering and Leaving signatures will have common traits across many locations. Motion signatures may take into account speed, motion cues, such as gait and/or size of a moving object which may also be stored in the dictionary. A primary user 22 may be asked to identify moving objects or blobs during the learning/onboarding phase, and later when unidentified moving blobs are detected. The dictionary inclusion may be based on term frequency-inverse document frequency and/or K-means training, for example. Significant and commonly occurring features of interest (moving blobs) whose signatures may be stored in the dictionary include a door opening and closing, a person entering and leaving a room, a pet walking or running through a room, for example.

A second dictionary may be created to store features, such as colors, edges, corners, etc., which may also be extracted from video. This dictionary stores the "what" features of what is moving to recognize objects, such as people and pets, regardless of their motion or position in the video.

Feedback may be provided from the learning module 720 to the video processing module 713 during any one or all of the motion recognition, segmentation, or feature extraction steps, to improve the video processing based on the learning process and the success of identifying moving objects.

Video files and other data files containing data from other sensors may be sent by the device 10 to the system 14 with metadata including an identification of the device it is coming from, along an encrypted channel such as a secure socket layer (SSL) connection. In accordance with embodiments of the invention, the device 10 transmits audio, video and sensor data simultaneously. That is different than currently available home automation systems, for example, which may include multiple independent sensors. The device 10 may transmit a complete dataset, which facilities rapid response by the system 14. If there are multiple devices 10 operating in a home 12 or other location at the same time, they may work simultaneously to compile the varying sensor data to send to the system 14.

A current state of the device 10, including the current video file and current data from the sensors, such as temperatures, humidity, air quality, etc., may be stored in the database 20 in association with an identification of the device, the location of the device determined by geo-location, and the identification of the primary user. Prior states of the device 10 may also be saved in the database 20 or other such storage device or database to facilitate learning, for example. Backup contacts, family members, group members, and notification rules may also be stored in the database in association with the identification of the device 10 and primary user 22. In one example, video is stored in a separate database and a pointer or to the video is stored in association with the other status information.

Figure 23:
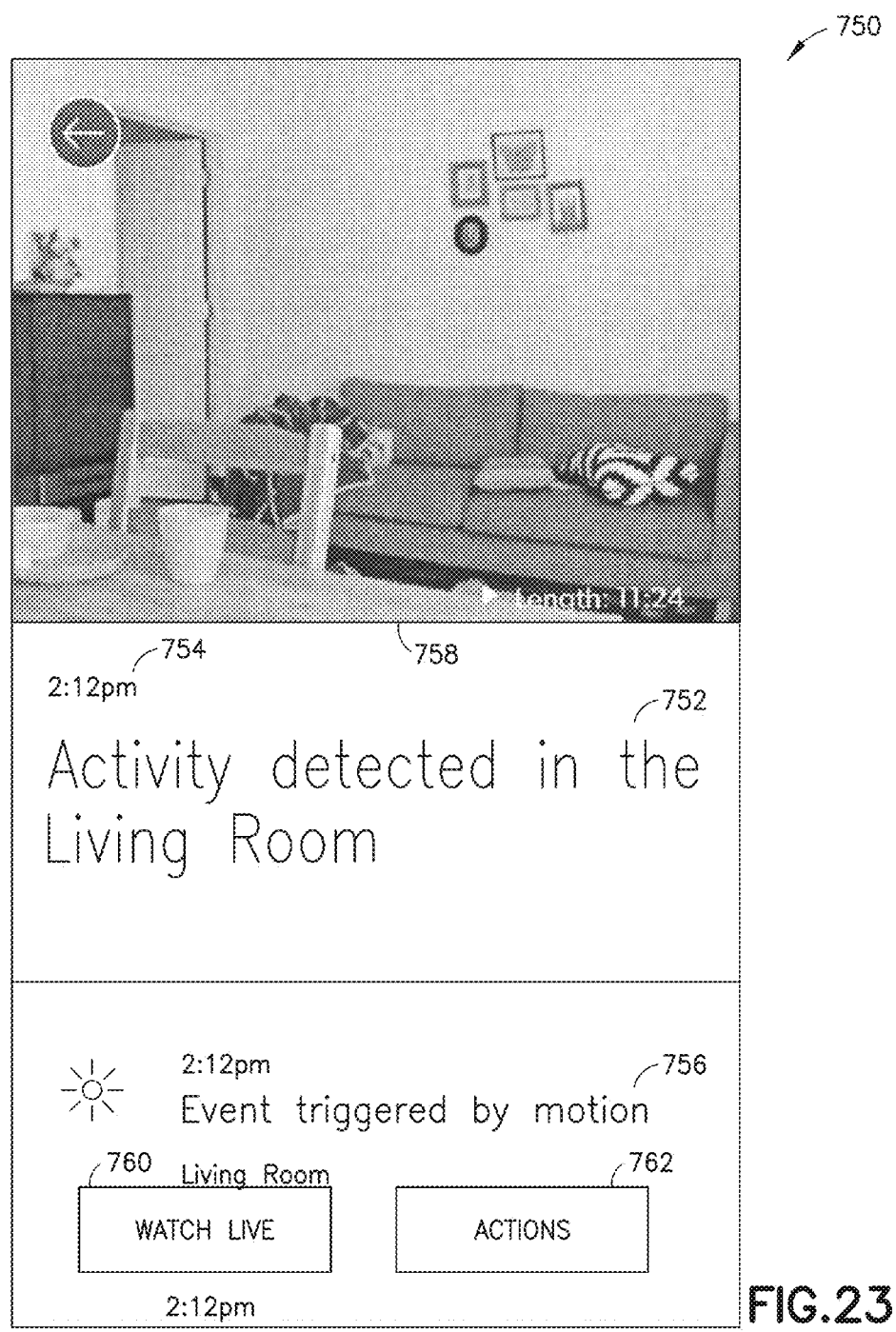
FIG. 23 is an example of a notification provided to user device of a primary user as displayed by the App, in accordance with an embodiment of the invention.

FIG. 23 is an example of a notification 750 provided to user device 24 of a primary user 22, as displayed by the App. The notification 750 includes a description 752 of the event and location where it took place. In this example, activity was detected in the living room. The notification also includes the time 754 of the event, here 2:12 PM. The notification 750 also describes what triggered the event 756, here motion detection. An image 758 of the room where the event took place is also shown. Clicking on the image plays a video of the event. An icon 760 is also provided, which enables viewing a current video of the room where the activity took place. Another icon 762 is provided to provide action options for the primary user 22. The action options may include clearing the event as a false alarm, contacting a backup contact 26, or contacting the police 28, fire department 30, or an ambulance 32, for example.

Figure 24:
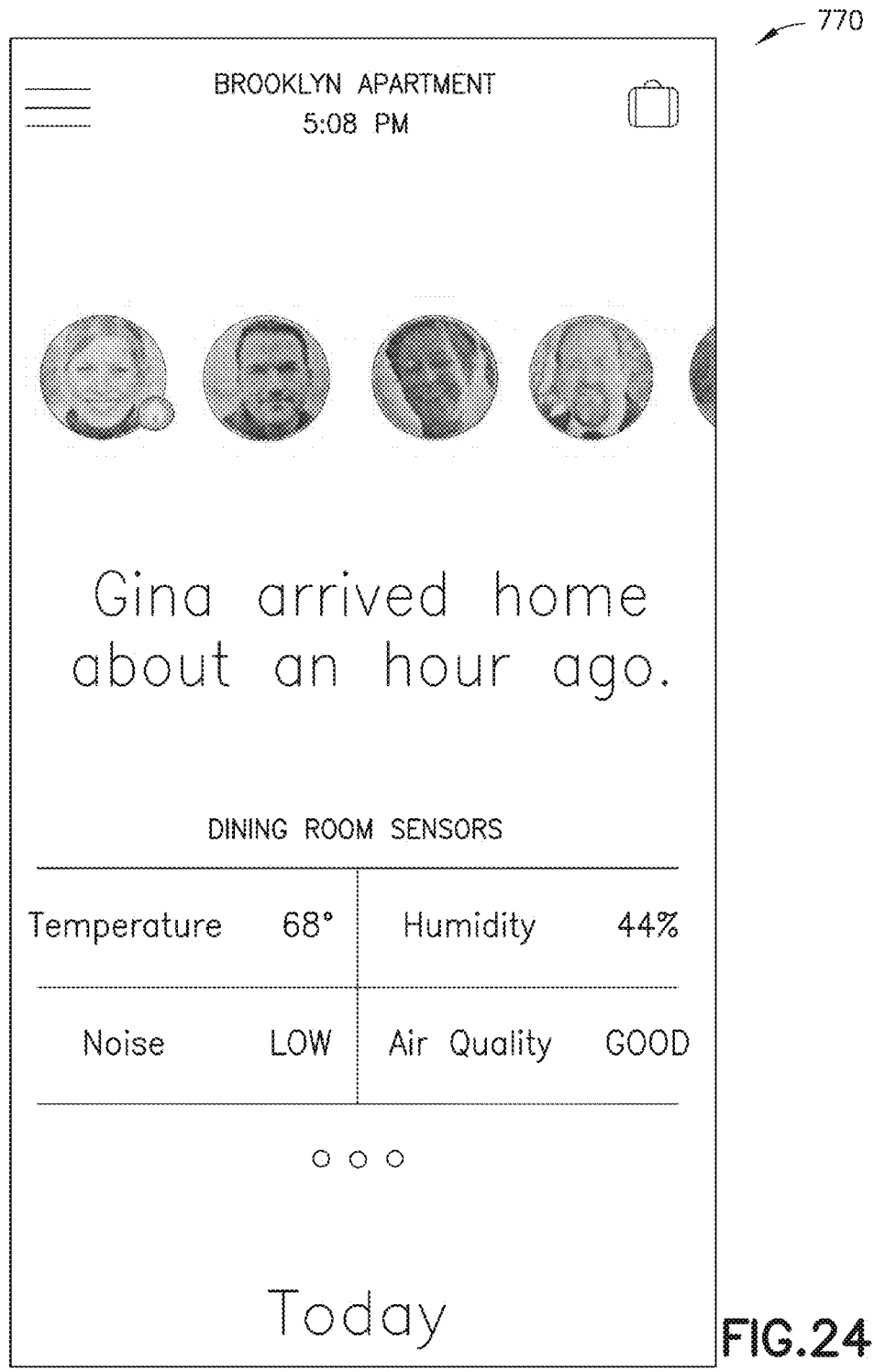
FIG. 24 is an example of a notification displayed on a user device that states that a person arrived home and when, in accordance with an embodiment of the invention.

FIG. 24 is an example of a notification 770 displayed on a user device 24 that states that a person arrived home and when. The notification also includes the current temperature, humidity, air quality, and noise in the room based on the T/H sensor 90/88, the air quality sensor 94, and the microphone 76, respectively.

Gesture and Sound-Based User Inputted Actions

As discussed above, the primary user 22 can control the device 10 through an App from their smart phone or a web interface. The device 10 can also be controlled by the user through active and passive actions. Active actions that can control the device include voice commands and physical gestures, for example. A combination of voice/sound and gesture actions can also generate a command to control the device. Sound may be detected by the microphone 76 and gestures may be detected by the image sensor 60. In one example, a primary user or other member of a household can call out for a security alert to contact authorities, such as the police or fire department, or to contact a backup user, for example. A specific action can be tailored based on the desired outcome, such as a user designating a verbal command to issue a low level alert or a specific hand gesture to issue a high level alert. Voice recognition technology may be used to teach the system to recognize commands, as is known in the art. Gesture recognition technology may be used to recognize gestures, as is also known in the art.

The user can also control the device through passive actions. Movement and video cues determine passive actions. In one example, the primary user can walk in front of the device 10 to cause the device to disarm after the device and/or system 14 recognizes the primary user through facial recognition, for example. The device 10 can also sense directional based input from its image sensor 60 to indicate whether a particular movement is normal or out of the ordinary.

Timeline

When an event is stored by the system 14 and/or the device 10, it may be shown to the user in a 'timeline' of activities in their location. A timeline is a linear, chronological schedule of events that occurred in a given location over a time period that have been captured by the device 10 or multiple devices 10 in a location. The timeline is displayed on a user device 24 via the App, based on information provided to the user device from the system 14 and/or the device 10, via the network 16. The timeline allows a primary user 22 to quickly get an overview of all activity in a user defined location that is captured by the device or devices 10. The timeline allows a user to toggle between events and previous notifications, under the control of the App.

The timeline may be composed of two types of events, engagement entries and event entries, for example. Engagement notifications are generated when a primary user 22 or other user, such as a family member (trusted user), interacts with the device 10. Event notifications are generated when the device 10 is armed and detects something out of the ordinary.

Engagement entries capture the engagement of a user at a particular location with the device 10. For example, an engagement entry is generated when a primary user arrives or departs from home. Other engagement notifications include device mode changes, whether initiated by the system automatically or by a primary user 22 (e.g. "device is now armed") or (e.g. "Amber disabled device"), a primary user goes live (explained in further detail below), a primary user makes changes to notification settings (e.g. "Justin paused all notifications for one hour"); or when a primary user resolves an Event, as described below.

The timeline also allows a user to manage event notifications. For example, the primary user 22 may see which sensors triggered event creation; learn which device in the home triggered event creation, in the case of multiple devices in a single location; learn at what time an event triggered; see video clips from when other primary users went "live" (actively used the camera to record remotely); see who went live, at what time, and from where (via GPS location); see the severity of an event; leave comments on entries for other users with access to the timeline; see how the event was responded to, and by which user; see sensor readings to make sure my environment is normal; see a high level view, and a detailed view of each event; see sensor details for each event; learn which users were home during each event; learn how long each event lasted; watch video from an event; know the status of notifications from an event; share an event socially; download an event report (sensor data, event timeline, video, etc.); mark an event as important; email or text an event video and details; and/or leave feedback for other users with access to the timeline.

The timeline may include events where the device 10 notified the primary user 22 of potential security threats. The timeline may also include events that did not result in notification to the primary user 22, due to learning that the primary user does not want to be notified of a particular event, or due to lack of severity of the event, for example.

Figure 25:
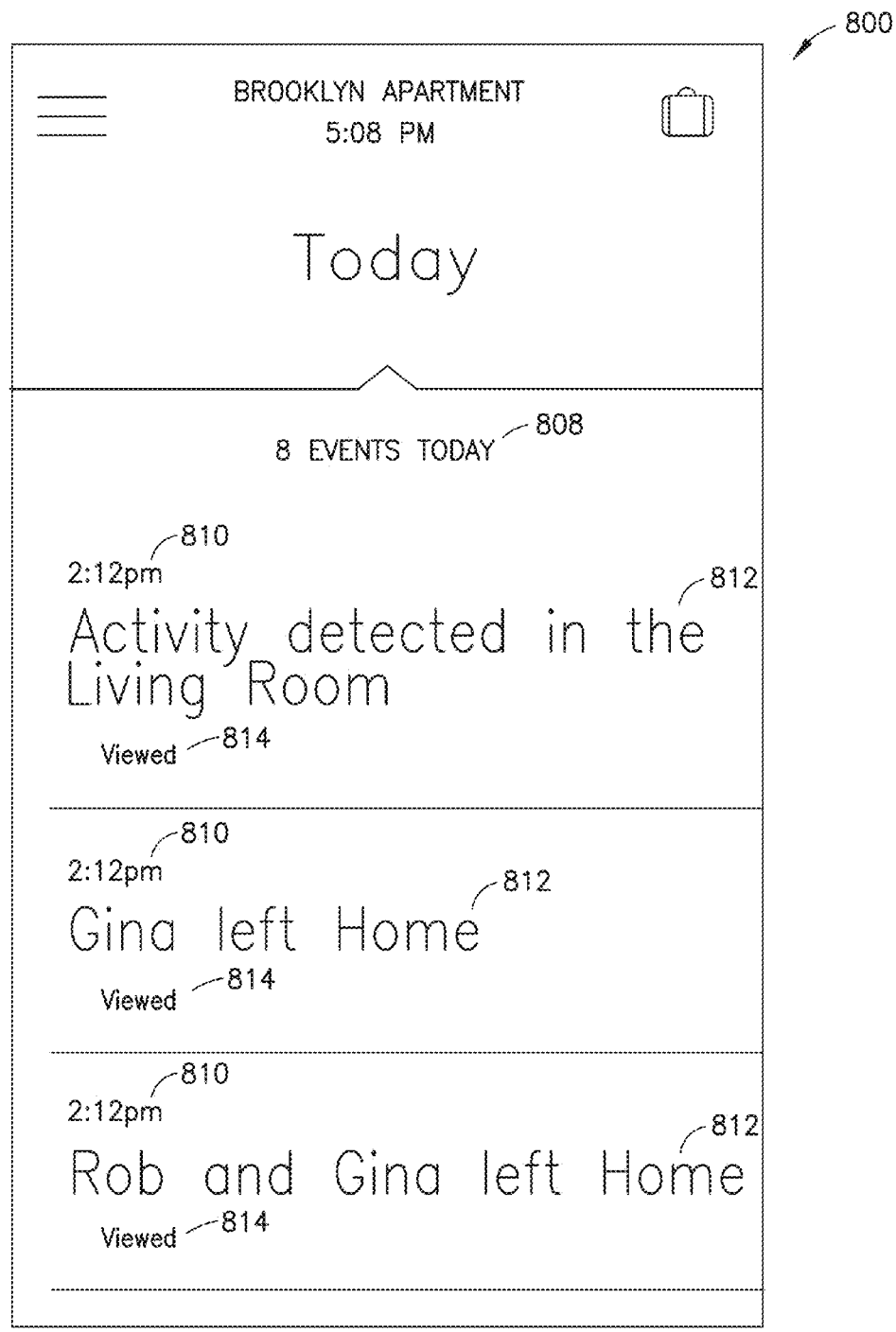
FIG. 25 is an example of a timeline of events that can be displayed by the user device via the App, from data received from the system and/or the device, in accordance with an embodiment of the invention.

FIG. 25 is an example of a timeline 800 of events that can be displayed by the user device 24 via the App, from data received from the system 24 and/or the device 10. The timeline identifies the location 802 of the device 10, here "Brooklyn Apartment," the current time 804, the date (Today) 806, and the number 808 of events that took place so far that day (8). Three events are listed with the time 810 of each event and a summary 812 of the event. The timeline 800 may be scrolled by the user to see the additional events that are not currently displayed. The timeline also indicates whether the event was previously viewed 814.

FIG. 26 is a timeline 820 of notifications. Two days of notifications are shown, and the timeline may be scrolled to display additional notifications.

In the case of multiple primary users 22 sharing one or more devices 10, each user's timeline may appear slightly different and may be customized to them. Backup contacts 26 and other parties may have access to the timeline, if allowed by the primary user 22.

This concept of a timeline of your life within a physical location tailored specifically to what is normal or out of the ordinary for an individual user summarizes what is happening in one physical place from a sensor perspective, acting in close coordination with the camera/image sensor 60, microphone 76, and other sensors. For example, the device 10 and the system 14 knows who is in a certain location (using geolocation services on a mobile device that is linked to the account, facial recognition, and/or user patterns), what the temperature and humidity is inside based on the T/H humidity sensor 90/88 and outside via publically available weather information, what noise and activity is occurring via the microphone 76 and other sensor, and if all of these activities are normal or not. The activities, plus their relative 'normalcy' or 'non normalcy' can be outlined on a timeline, where the primary user 22 can quickly delve into each event to understand if and how it impacts their life, and can be notified for the events that are not normal occurrences.

The device 10 and/or the system 14 may also provide a 'day' or 'week in the life' summary of what happened in a given location, to provide a very rapid video clip view and understanding of what was happening in the location for that week. The user may be e-mailed a video clip synopsis of the week, the day, or other time period.

Primary users 22 may also access their devices 10 from any of their locations, to watch live streaming video from that device, enabling them to "Go Live." They can also see current sensor readings from the location and who is home/away at the time. The primary user 22 has the option to save the video clip and corresponding sensor data.

A clip library allows users to store flagged video clips that they want the system 14 to store for them. These can include clips of events they have been notified to a clip of a robbery may be later used in court or for a police report. The user may request that clips of happy events, such as such as light hearted clips of the family pet doing something noteworthy, for example, also be saved. Flagging a clip via the App saves that clip for them in the database 20 or other storage device on the system 14. A clip library belongs to a location. Primary users may share saved clips from their clip library to social networks, such as Facebook and Twitter, for example.

Figure 27:
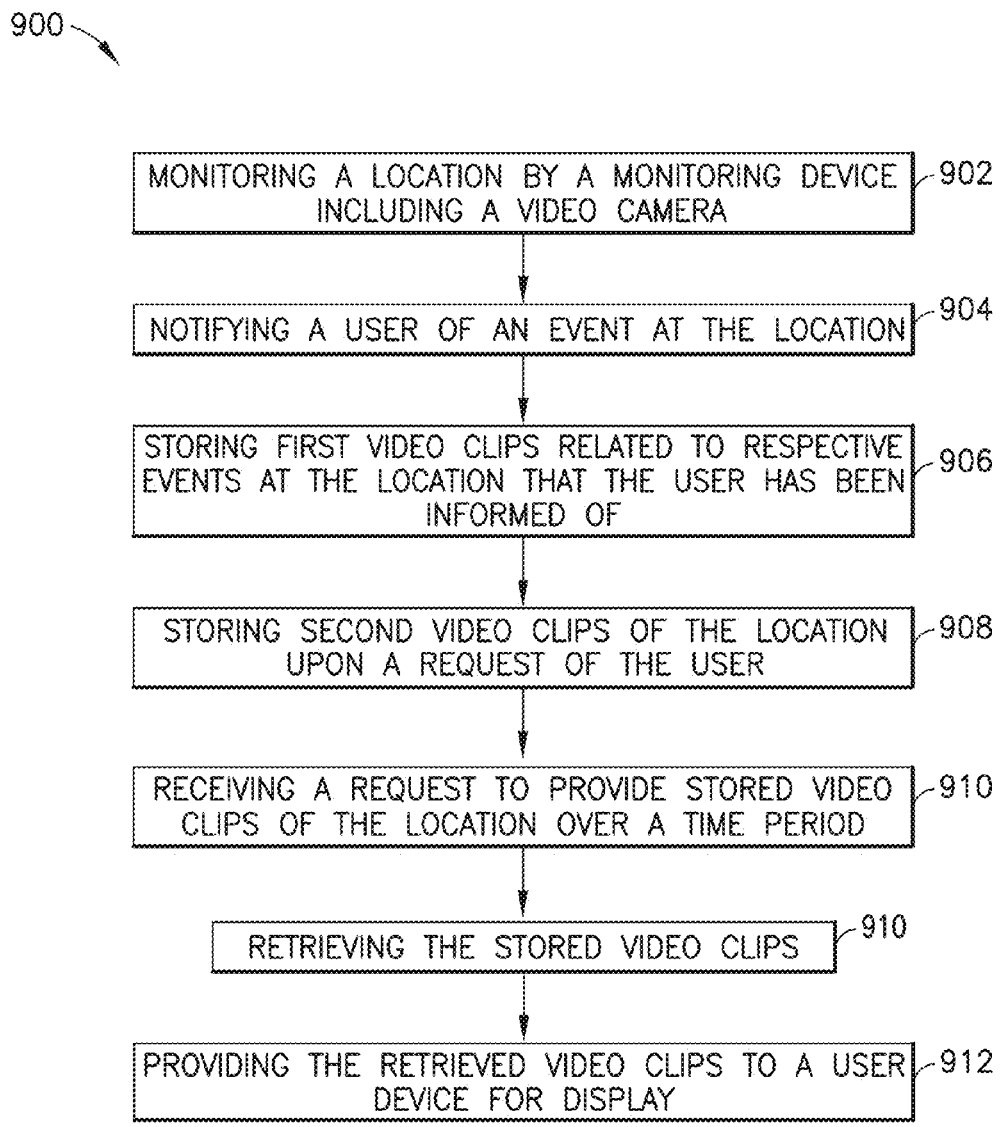
FIG. 27 is a flowchart of an example of a method for obtaining video clips from the system, in accordance with an embodiment of the invention.

FIG. 27 is an example of a method 900 for generating a day or week in the life at a location. A location is monitored by a monitoring device 10 including a video camera, such as an imaging sensor 60, in Step 902. A primary user 22 is notified of an event at the location, in Step 904. The user may be notified by the system 14, as discussed above. Video clips related to respective events at the location the user has been informed of are stored, in Step 906. The video clips may be uploaded to the system 14 by the device 10, as discussed above. The video clips may be stored in the database 20 or other storage device, by the system 14, in Step 906.

Video clips are stored by the system 14 upon a request of the user, in Step 908. The user 22 may request that particular video clips be stored via the App on the user device 24.

The system 14 receives a request from the user 22 to provide stored video clips over a designated time period, via the App, in Step 910. The system retrieves the stored video clips, in Step 910, and provides them to the user for display on the user device 24, in Step 912. The video clips may be compiled into a single file and sent via email, for example. The App opens and displays the video, when requested by the user 22.

Sensor Data Trends

The App also allows users to view sensor data trends from the sensors in the device 10, so that the primary user 24 is able to view visualized data about specific sensors within their location. For instance, if an air quality sensor is triggered, a graph may be generated by the system 14 and sent to the primary user 22 that indicates a measure of the air quality, a video and audio clip of when the sensor went off, a historical chart of what the air quality was before the alert, instructions (e.g. go outside, open windows, etc.), and action calls (press here to call poison control, etc.).

Over time, insights concerning environmental sensor data developed by the system 14 may also be sent to respective primary users 24. The sensor data may be benchmarked against average readings as determined by sensor data from similarly situated primary user 24. For example, "your temperature is an avg. of 76 degrees when no one is home." Most homeowners in your city keep their interior temperature around 70 degrees when no is home. Primary users 22 may also be able to see sensor data and compare it against a previous time frame (i.e. this month versus last month). Primary users 22 may also have the ability to toggle between data from specific sensors, showing graphs for those sensors that are relevant to them and hiding sensor data and corresponding graphs that are of no interest to them.

Geo-Location

Geo-location may be used to identify who is approaching, entering, or leaving a location, for example. Geo-location may also be used to provide an input into the device 10 and/or the system 14 to determine the location of the primary user 22 and other persons, such as family members, for example. Geo-location services are available in most smart phone or smart mobile devices. Disarming and arming of the device 10 and the system 14 may be based on geo-location. For example, the device 10/system 14 may be disarmed from issuing a notification that a person is approaching or entering a monitored location, when the primary user 22 is determined to be at or near the location, if desired by the user. In this example, while notifications are not sent, data may still be collected. Similarly, when the primary user 22 is determined to be leaving a location, the device 10/system 14 is armed to provide notifications, if desired by the user.

When a primary user 22 begins to approach a select radius around their home 12 or other location where the device 10 is located, it will send a signal to the home network that the user is in the area and be 'ready' for them to enter. This being 'ready' informs the device 10/system 13 not to notify the user/s immediately upon entry to alert of movement alarm, since the person entering the location is likely the user and thus it should wait another predetermined set of time (e.g. 45 seconds) to confirm the user is in the location through the App or wireless network and disarm itself, for example.

Geo-location of other users designated by the primary use 24, such as family members, for example, may also arm or disarm that device 10/system 14 without alerting the user. Such information may be saved into a 'timeline' but need not result in a notification as a security incident.

By geo-locating user device 24, other preferences in the home 12 may also be controlled. For example, preferences may be different depending on who is in the home. From a security and safety point of view, specific actions and notifications can align with the geo-location of phones and the confirmation of the proximity of individuals within the location. An individual owner of the account can set preferences for the individuals. An action may be a specific notification. For example, if the location of a primary user's child, for instance, is activated, then the primary user 22 can receive a timeline or graph of the activities of the child.

Geo-location may be performed in a variety of ways. In one example, a user device 24, such as a mobile device, may monitor a large region (~1 Km) centered around the user's home 12 using GPS coordinates, for example. When the user device 24 recognizes that it has entered this large region, it begins to search for a smaller region called an iBeacon, which are mini geo-fences that are created using BTLE devices. When the user device 24 recognizes the iBeacon, it sends a HTTPS request to the system 14 to disarm notifications.

In another example, when a mobile user device 22 recognizes that it has entered a large monitored region, it begins to search for the device 10, which is a Bluetooth low energy device. When connected to the user device 24, the BTLE device 10 becomes a peripheral device and the user device 24 becomes the central device. The user device 24 continues to search for the peripheral in the background. When the user device 24 detects the peripheral, it verifies that it is that user's device 10 and sends a HTTPS request to the system 14 to disarm notifications.

A secondary user, who can either be a primary user 24 of another device 10 or provisioned to be a backup/contact 26 in a group of the primary, can likewise be used to arm and disarm the security and notifications of the device, based on the criteria as set by the primary user 22.

Third Party Information and APIs

In accordance with another embodiment of the invention, the system 14 may enable connection between the system to and third parties, such as Facebook or LinkedIn, to learn the location of a user, and to learn who may be potential backup contacts, for example. If a user connects their Facebook account to the system 14, the system can scan the images of all of their friends in Facebook and ask the primary user whether they should be designated as backup contacts 26, for example. Based on the scanned images, the device 10 and the system 14 may be able to recognize the friends on Facebook if they enter the home 12 by matching an image or video captured by the image sensor 60 and comparing it to the scanned image, for example. The primary user 22 can then be informed of who entered their home 12.

In accordance with another embodiment of the invention, the system 14 may create an API to allow for the public and/or other users of their own device 10 to gather both generalized, anonymized data as well as specific data on individual's lives, in order to better understand their own environment. This open security platform can be used by other security companies who wish to make devices to connect to the system 14 and/or to use the aspects of the system 14 for other security or non-security related benefits.

Other third party information that may be obtained and used by the system includes weather. For example, temperature, humidity, and air quality thresholds may be changed by the system 14 based on the local weather, for example.

Local crime warnings may also be used by the system 14. For example, the system 14 may send notifications to primary users 22 under circumstances where the user preferences state that notifications should not be provided, if it known that crime has recently increased in the area, for example.

Community Watch

Another embodiment of the invention is the interaction between the system 14 and the user's social group/friends, family or neighbors that they choose to include in the system. The primary user 22 may designate through the App on the user device 24 individuals who the primary user knows as their 'social group,' and identifies those users as backups to the primary user notification. These backups are placed in specific 'groups', which work together to look into each other's homes from a timeline perspective and help monitor each other's safety and security. The system 14 may also automatically designate people identified as friends of the primary user 22 on Facebook, for example.

These groups can be anywhere from 2 people to 10 people or more, but are intended to be a small social circle that enables a community of people to respond from a security point of view. Member of the groups receive the notifications from the system 14/device 10 either after the primary user 22 or, in the case of high priority notifications, at the same time as the primary user. This enables a crowd sourced response, where multiple people may respond the notification to ensure that there is an accurate and rapid response to the system. Additionally, a primary user 22 can cede primary user status and provide temporary "keys" to pass ownership and control over the software and hardware that make up the device over a pre-determined period of time. These digital keys would allow a recipient to have temporary access to the device 10 when someone other than the primary user would be in or using the home, such as when renting out a primary user's home to a temporary guest or to give access to a friend of family member to check on a primary user's home when they are on vacation.

In another example, if a primary user 22 does not respond to a notification, after a predetermined length of time, the notification would be sent to some or all member of the group by the system 14, for example. Members of the group may be able to either see what is going on in the location, or to see a written description of what caused the notification, for example. The primary user 22 may determine how much information members of the group receive by setting appropriate preferences. Multiple group member can then work together to resolve an incident, as a virtual neighborhood or virtual community watch, and share in the responsibility of responding and reacting to a security or safety-related incident.

Individuals within the primary user's social group can take direct or indirect action through the App to resolve an incident or respond to the incident or event. A primary user 22 may be a member of multiple groups. A group may comprise two users, or a home owner and a secondary family member in their location or in another location, for example. The group members may also have access to the timelines of other members in the group, and may add or subtract members from the group (depending on group settings and preferences). The groups are a way for people to bring along people that they know and trust already to help them do security or safety, such as their parents, children, neighbors, and friends.

In addition, a group could comprise some or all of the inhabitants of a physical building of part of a building, such as an apartment building or office. This group may share limited information, such as confirmed incidents, or temperature, humidity and air quality readings. Multiple members of the building or office would share the feed to the device/s in the office, and share in the notifications or response. Knowing what is going on in their physical location would be beneficial to all members of the group. A person can be a member of the group, even if they have no device or no membership. For example, they can be someone's backup, and still have the ability to participate in other people's security. In this case, they may not, however have an input of their own.

A group may also be a community and may include an input for the police or other authorities. Members of the group would receive instant notification should someone or something either be confirmed by the owner, or should a high heat, carbon monoxide or other life-safety related event be detected. Appropriate government authorities or non-governmental support companies/entities can be contacted directly or indirectly from the device 10 and/or the system 15 to inform/report an incident if the incident is deemed out-of-the-ordinary. Alternatively, the device 10/system 14 may be configured by the primary user 22 to alert authorities if notifications remain unacknowledged by the primary user or group members.

A second layer aside from clusters of neighbors watching over each other is the interaction between the system 14 and local authorities. A dedicated software App or website leading to police and other authorities could feed data collected by devices 10 data concerning crime and other safety information directly from a user's home to relevant groups. Appropriate government authorities or non-governmental support companies and entities can be contacted directly or indirectly from the device 10 or system 14, to inform and report of an incident that is deemed out-of-the-ordinary. Alternatively, the device 10 and/or system 14 can be configured by the primary user 22 to alert authorities if notifications remain unacknowledged by the primary user or group members, by setting appropriate settings.

The User App

As discussed above, the primary user 22 and other users, if allowed by the user, may communicate with the device 10 and system 14 via their mobile device or other processing device, such as a laptop or desk top computer, through an Application in the device. From the App, a user controls the settings for the device, receives notifications when something occurs that is out of the ordinary, and has the ability to respond in an appropriate fashion. The features of the mobile application work in concert to provide a holistic view of what occurs in one's home and the necessary tools to effectively monitor one's home in different situations.

Specific notifications are transmitted to the user on their mobile device, tablet, computer, or other web-connected device. The messages can be sent via email, phone, text, or in-App message based on user preferences. Based on the input from the device 10 and the system 14, notifications or alerts are pushed to the user to apprise them of relevant incidents generated by the system.

Other types of notifications include device notifications. These are notifications related to the system that are not generated by human interaction. For example, a device notification would be sent to a user if the system loses power or if the system is disconnected from the Internet. There are also several classes of notifications that would be sent to a user that are not related to device functionality. These are non-device, non-human interaction, generated notifications such as: third party weather information; a reminder to pay for service plan; a notification that allotted data storage reaching capacity; SDK/API related notifications; software updates; confirmation of backup invitations; when notifications escalate to a backup contact; and/or confirmation of additional user notifications.

Custom Modes

The device 10 and system 14 may operate differently in different modes of operation. The modes of operation may include a home mode, an array mode, a nighttime mode, a privacy mode, and/or a vacation mode. Modes may be changed directly on the device 10 via the capacitive switch 114 and/or via the App in the user device 24, for example. Each mode may be represented by a color displayed by the RGB LED 96, for example.

During Night Time Mode, the device 10 and the system 14 can be enabled to still watch over a user's home without notifying a user of every instance of an event. For example, a user can set Night Time Mode to only receive critical alerts, such as when the device 10 detects movement or a high spike in temperature, for example, and have all other alerts be delayed until the next morning, during set up or at a later time.

In vacation mode, the device 10 and the system 10 may be in high alert mode. For example the system can automatically sound the siren 86 when motion is detected instead of waiting for a user, or backup contact, to resolve the event. Additionally, escalation preferences are suspended with the primary user 22 and backup contacts receiving notifications simultaneously.

In addition, in vacation mode, a primary user may cede primary user status and provide temporary digital "keys" to pass ownership and control over device 10 and the system 14 to the backup contact or other party for a pre-determined period of time.

These digital keys would also allow a recipient to have temporary access to the device 10 in instances where someone other than the primary user would be in or using the home. For example, when renting out a primary user's home to a temporary guest or to give access to a friend of family member to check on a primary user's home when they are on vacation.

The examples of embodiments of the invention described herein are merely exemplary and one of ordinary skill in the art will recognize that aspects of the described embodiments may be changed without departing from the spirit and scope of the invention, which is defined in the claims below.

We claim:

1. In a system comprising a security monitoring device in a monitored physical location, a security processing system configured to communicate with the security monitoring device over a network, and one or more mobile devices configured to communicate with the security monitoring device over the network, a method comprising:
   arming and disarming the security monitoring device and the security processing system device based on geolocation data associated with at least one of the mobile devices,
   wherein the disarming comprises:
      recognizing, with a particular one of the mobile devices, when the particular mobile device enters a first region centered around the monitored physical location;
      when the particular mobile device enters the first region, searching for a second region that is smaller than the first region and is defined by a geo-fence;
      when the mobile device recognizes the geo-fence, sending a request from the particular mobile device to the security processing system to disarm the system from sending certain notifications to users of the system; and
      processing the request at the security processing system, in conjunction with at least one user-provided instruction and geolocation data from any one or more of the other mobile devices in the system, to set system behavior with respect to notifying articular users of safety or security-related events at the monitored physical location and saving data about the events at the monitored physical location to one or more user-accessible timelines showing information about past events at the monitored physical location.

2. The method of claim 1, further comprising providing the geolocation data with a geolocation service in the particular mobile device.

3. The method of claim 1, wherein the disarming notifications comprises:
   disarming from issuing a notification that a person is approaching or entering the monitored physical location, when a primary user is determined to be at or near the monitored physical location based on the geolocation data.

4. The method of claim 3, wherein the primary user is a person who resides at the monitored physical location or is otherwise associated with the monitored physical location and who interacts with the security monitoring device and/or the security processing system on a regular basis.

5. The method of claim 3, wherein data is collected by the security monitoring device/security processing system even when the security monitoring device/security processing system is disarmed from issuing the notification that the person is approaching or entering the monitored physical location.

6. The method of claim 3, further comprising:
   arming the security monitoring device/security processing system to provide notifications when the primary user is determined to be leaving the monitored physical location.

7. The method of claim 1, further comprising:
   generating a signal when a user begins to approach a selected radius around the monitored physical location, wherein the signal is to ensure that the security monitoring device/security processing system will not notify the user or other users immediately upon an entry into the monitored physical location, but instead will wait a predetermined amount of time after the entry into the monitored physical location to confirm that the user is in the location either through a software-based application or a wireless network, and, upon confirmation, will disarm.

8. The method of claim 1, further comprising creating the geo-fence using a Bluetooth Low Energy (BTLE) device.

9. The method of claim 1, wherein the geolocation data is associated with the mobile user device of a primary user or the mobile user device of a secondary user, wherein the primary user is a person who resides at the monitored physical location or is otherwise associated with the monitored physical location and who interacts with the security monitoring device and/or the security processing system on a regular basis, and wherein the secondary user is a person who has been designated as a backup contact to receive notifications from the system in circumstances determined by the primary user.

10. The method of claim 1, wherein the security monitoring device comprises:
a housing;
a camera supported by the housing and configured to collect video of the monitored physical location;
a temperature sensor supported by the housing and configured to detect a temperature associated with the monitoring physical location;
an air quality sensor supported by the housing and configured to sense a quality of air in the monitored physical location;
a computer-based processing device; and
a Bluetooth antenna, and
wherein the security processing system comprises:
a processing device; and
a database,
the method further comprising:
collecting data about the monitored physical location with at least the camera, the temperature sensor and the air quality sensor, and
if, based on the collected data, the security monitoring device or the security processing system determines that an event has occurred in the monitored physical location that may be of interest to a user, then presenting a notification to the user at an associated one of the mobile devices.

11. In a system comprising a security monitoring device in a physical location, and one or more mobile user devices configured to communicate with the security monitoring device over a network, a method comprising:
arming and disarming certain security features and/or sensors of the security monitoring device based on geolocation data associated with at least one of the mobile user devices,
wherein the disarming comprises:
recognizing, with a particular one of the mobile devices, when the particular mobile device enters a first region centered around the monitored physical location;
upon the particular mobile device entering the first region, searching, with the particular mobile device, for a second region that is smaller than the first region and that is defined by a geo-fence;
sending a request from the particular mobile device to an associated computer processing system when the particular mobile device recognizes the geo-fence, wherein the request is to disarm the system from sending notifications to one or more users of the system; and
processing the request at the associated computer processing system, in conjunction with at least one user-provided instruction and geolocation data from any one or more of the other mobile devices in the system, to set system behavior with respect to notifying particular users of safety or security-related events at the monitored physical location and saving data about the events at the monitored physical location to one or more user-accessible timelines showing information about past events at the monitored physical location.

12. The method of claim 11, further comprising:
providing the geolocation data with a geolocation service in one or more of the mobile devices.

13. The method of claim 11, further comprising:
disarming the security monitoring device from issuing a notification that a person is approaching or entering the monitored physical location, when a primary user is determined to be at or near the monitored physical location based on the geolocation data.

14. The method of claim 13, wherein the primary user is a person who resides at the monitored physical location or is otherwise associated with the monitored physical location and who interacts with the security monitoring device and/or an associated security processing system on a regular basis.

15. The method of claim 13, further comprising:
collecting data by the security monitoring device or an associated security processing system even when the security monitoring device is disarmed from issuing the notification that the person is approaching or entering the monitored physical location.

16. The method of claim 13, further comprising:
arming the security monitoring device to provide the notification when the primary user is determined to be leaving the monitored physical location.

17. The method of claim 11, further comprising:
generating a signal when a user begins to approach a select radius around the monitored physical location, wherein the signal is generated to ensure that the security monitoring device and/or an associated security processing system will not notify the user or other users immediately upon the user's entry into the monitored physical location.

18. The method of claim 11, wherein the geo-fence is created using a Bluetooth Low Energy (BTLE) device.

19. The method of claim 11, wherein the geolocation data is associated with the mobile user device of a primary user or the mobile user device of a secondary user,
wherein the primary user is a person who resides at the monitored physical location or is otherwise associated with the monitored physical location and who interacts with the security monitoring device and/or an associated security processing system on a regular basis, and
wherein the secondary user is a person who has been designated as a backup contact by the primary user.

20. The method of claim 11, wherein the security monitoring device comprises:
a housing;
a camera supported by the housing and configured to collect video of the monitored physical location;
a temperature sensor supported by the housing and configured to detect a temperature associated with the monitoring physical location;
an air quality sensor supported by the housing and configured to sense a quality of air in the monitored physical location;
a computer-based processing device; and
a Bluetooth antenna, and
wherein the security processing system comprises:
a processing device; and
a database,
the method further comprising:
collecting data about the monitored physical location with at least the camera, the temperature sensor and the air quality sensor, and if, based on the collected data, the security monitoring device or the security processing system determines that an event has occurred in the monitored physical location that may be of interest to a user, then presenting a notification to the user at an associated one of the mobile devices.

21. The method of claim 1, further comprising:
determining that a primary user of the system is at or near the monitored physical location;
disarming the system from issuing a notification that a person is approaching or entering the monitored physical location when a primary user of the system is determined to be at the monitored physical location; and
ceasing to issue notifications, but continuing to collect data, when the system is disarmed from issuing notifications.

22. The method of claim 1, further comprising:
enabling a primary user of the system to designate one or more other users of the system, such that geolocation data associated with the one or more other users of the system arms or disarms the system, without notifying the primary user.

23. The method of claim 1, further comprising controlling other system preferences associated with the monitored physical location depending on who is in the home based on geolocation data.

24. The method of claim 1, wherein there are multiple system users associated with the monitored physical location, each of which has a corresponding one of the one or more mobile devices.

25. The method of claim 24, wherein specific system actions and notifications align with geolocation data associated with each respective one of the one or more mobile devices.

26. In a system comprising a security monitoring device in a monitored physical location, a security processing system configured to communicate with the security monitoring device over a network, and one or more mobile devices configured to communicate with the security monitoring device over the network, a method comprising:

arming and disarming the security monitoring device and the security processing system device based on geolocation data associated with at least one of the mobile devices, wherein the disarming comprises:

generating a signal when a user begins to approach a selected radius around the monitored physical location, wherein the signal is to ensure that the security monitoring device/security processing system will not notify the user or other users immediately upon an entry into the monitored physical location, but instead will wait a predetermined amount of time after the entry into the monitored physical location to confirm that the user is in the location either through a software-based application or a wireless network, and, upon confirmation, will disarm.

\* \* \* \* \*